(12) United States Patent
Snyder

(10) Patent No.: US 7,126,879 B2
(45) Date of Patent: Oct. 24, 2006

(54) MEDICATION PACKAGE AND METHOD

(75) Inventor: William B. Snyder, Wrightsville, PA (US)

(73) Assignee: HealthTRAC Systems, Inc., Wrightsville, PA (US)

( * ) Notice: Subject to any disclaimer, the term of this patent is extended or adjusted under 35 U.S.C. 154(b) by 436 days.

(21) Appl. No.: 10/796,224

(22) Filed: Mar. 9, 2004

(65) Prior Publication Data

US 2004/0178112 A1 Sep. 16, 2004

Related U.S. Application Data

(60) Provisional application No. 60/453,297, filed on Mar. 10, 2003.

(51) Int. Cl.
  G04B 47/00 (2006.01)
  B65D 83/04 (2006.01)
(52) U.S. Cl. .................. 368/10; 206/531; 206/534; 206/807
(58) Field of Classification Search ............ 206/528, 206/530, 531, 534, 459.1, 807; 116/307; 340/309.3, 309.7, 309.8, 573.1, 573.3; 368/10
See application file for complete search history.

(56) References Cited

U.S. PATENT DOCUMENTS

| | | | |
|---|---|---|---|
| 4,258,354 A | 3/1981 | Carmon et al. | |
| 4,616,316 A | 10/1986 | Hanpeter et al. | |
| 4,617,557 A | 10/1986 | Gordon | |
| 4,662,537 A | 5/1987 | Wolf et al. | |
| 5,159,581 A | 10/1992 | Agans | |
| 5,408,443 A | 4/1995 | Weinberger | |
| 5,412,372 A | 5/1995 | Parkhurst et al. | |
| 5,646,912 A | 7/1997 | Cousin | |
| 5,852,408 A | 12/1998 | Christiansen et al. | |
| 5,915,589 A | 6/1999 | Lim | |
| 5,995,938 A | 11/1999 | Whaley | |
| 6,163,736 A | 12/2000 | Halfacre | |
| 6,198,383 B1 | 3/2001 | Sekura et al. | |
| 6,294,999 B1 | 9/2001 | Yarin et al. | |
| 6,330,957 B1 | 12/2001 | Bell-Greenstreet | |
| 6,380,858 B1 | 4/2002 | Yarin et al. | |
| 6,411,567 B1 * | 6/2002 | Niemiec et al. | 368/10 |
| 6,415,202 B1 | 7/2002 | Halfacre | |
| 6,574,165 B1 | 6/2003 | Sharma et al. | |
| 6,574,166 B1 * | 6/2003 | Niemiec | 368/10 |
| 6,839,304 B1 * | 1/2005 | Niemiec et al. | 368/10 |

\* cited by examiner

*Primary Examiner*—Luan K. Bui
(74) *Attorney, Agent, or Firm*—Buchanan Ingersoll & Rooney PC; Dennis M. Carleton

(57) ABSTRACT

A child resistant medication package and associated system can enable compliance and anti-diversion features. The medication package can include a timing reminder, can detect and record a compliance history of each dose of medication, and can include anti-tamper capabilities to ensure doses are removed in the intended fashion. The medication package can have the capability to exchange data with other devices, including personal computers. The associated system can include a central database that receives data from the medication package, and provides for the transmission of data between various system locations, including not only the individual medication package, but also, for example, drug manufacturers, pharmacies, physician offices, law enforcement agencies, and a database managing agency.

50 Claims, 11 Drawing Sheets

MEDICATION PACKAGE AND METHOD

CROSS REFERENCE TO RELATED APPLICATIONS

This application claims priority to U.S. Provisional Patent Application Ser. No. 60/453,297, filed Mar. 10, 2003.

BACKGROUND

The invention generally relates to packages and containers for medication, and more particularly, to a medication package and associated method for anti-diversion detection and compliance monitoring.

Adherence to prescription medication dosing schedules is often problematic for both the patient and the physician. Forgetting to take medications, or non-compliance, results in poor patient outcome and often is not reported to the prescribing physician by the patient. This can result in the physician increasing the dosage or changing to a different class of medication because of apparent ineffectiveness. Conversely, the taking of medications too frequently, or abuse, can have dangerous consequences for the patient. There is also a problem with diversion of the medication. Hereinafter, "diversion" will be used to refer the diversion of a medication with abuse potential from the intended legitimate patient population to an illicit market. The non-medical use and diversion of prescription drugs such as opioids, stimulants and central nervous system depressants can lead to abuse, addiction, and even death. While doctors and pharmacists often attempt to assure medications are being dispensed and used as prescribed, diversion of medications to the illicit market has risen to unprecedented levels. Currently, there are no, or inadequate, effective measures in place to counteract the problems that allow diversion of medications with abuse potential.

It is well known that prescription drugs relieve symptoms for millions of people and allow those who suffer from chronic syndromes to lead productive lives. Unfortunately, non-compliance is common in many disease syndromes such as schizophrenia, depression and dementia. It is intuitive that non-compliance translates into additional cost to our health care system. Additionally, most people who use medications do so responsibly; however, the non-medical use of prescription drugs, especially pain medications, has become a serious public health concern. Non-medical use of drugs such as opioids, stimulants and central nervous system depressants can lead to abuse, addiction, and even death. Consequently, communities are finding their limited social and financial resources overwhelmed by the high cost of rehabilitating those who become addicted to one of these medications. In addition, crime rates have risen dramatically in those geographic areas endemic with abuse of these medications. According to the "National Household Survey on Drug Abuse," 1999, there were an estimated 4,000,000 people were using prescription drugs non-medically in that year. That survey found that, of these, 2.6 million misused pain relievers, 1.3 million misused sedatives and tranquilizers, and 0.9 million misused stimulants. Furthermore, this illicit diversion of medications has resulted in unnecessary expense to medical insurance carriers, a significant factor in our cost driven health care system. As provided in a 1999 report by the "Substance Abuse and Mental Health Services Administration" (SAMHSA), visits to hospital emergency departments due to abuse of one particular pain medication, hydrocodone, increased 37% from 1997 to 1999. Aside from the obvious problem addiction causes the patient, many of these cases also result in expensive litigation costs to the drug manufacturer, physician and the malpractice liability insurance carriers. While doctors and pharmacists currently attempt to assure medications are being dispensed and used as prescribed, diversion of medications to the illicit market has risen to unprecedented levels. The total cost to the U.S. economy associated with diversion of prescription medications is estimated to be 1.77 billion dollars annually.

Prescribing physicians and pharmacists have little at their disposal to prevent non-compliance, abuse, and diversion, other than the word of the patient that the medications are being sought and taken in a legitimate fashion and as prescribed. Patients, for example, who receive prescription drugs legitimately may inadvertently or intentionally take them too frequently, which may result in abuse or addiction. Additionally, a patient may obtain prescriptions for a pain reliever from multiple doctors simultaneously in an attempt to abuse the medication or sell it illegally. Known as "doctor-shopping," this practice continues because current prescription monitoring programs are inefficient and ineffective. At follow-up office visits the prescribing physician has no way of monitoring whether any doses were removed from the package ahead of time, which could suggest abuse or diversion is occurring. There are also reported cases of unscrupulous doctors financially motivated to wantonly write prescriptions or directly supply pain relievers to patients for cash. Other examples of diversion are theft of pain relievers by pharmacy employees, falsification of medication inventory by pharmacy employees and theft of prescription pads from doctors' offices.

According to a March 2001 report by "Alliance of States with Prescription Monitoring Programs," there are currently 17 states that have central prescription-monitoring (PM) programs. However these programs established to counteract diversion can be ineffectual due to multiple factors, such as, for example, the following:

The transfer of patient and prescription information from the pharmacy to the PM database at the time the medication is dispensed is manually entered by the pharmacist. This process is slow, inefficient, allows for human error with regard to data entry and is not in 'real-time'.

The current PM programs require months to process the data received from the pharmacies. The lack of a 'real-time' database allows diversion to continue because the dispensing pharmacy has no way of communicating with other pharmacies to determine, for example, if the patient had filled similar prescriptions obtained from different doctors that day.

Pharmacies are mandated by law to perform monthly inventories of all medications with abuse potential and report this data to the managing agency overseeing the PM program. This depends on the pharmacist entering truthful and valid inventory data, which is unlikely to occur if the pharmacists themselves are diverting the medications for profit.

Patients by law can only be prescribed one-month supplies, with no refills, of medications with abuse potential such as pain relievers or stimulants. This requires the patient to return to their doctor monthly for subsequent prescription renewals. The physician has no way of knowing at these follow-up office visits if the pills were taken as prescribed during the previous month. Currently, for example, a patient can remove all the pills from the bottle on the day the prescription is filled and sell them, or take them too frequently and become addicted.

There have been numerous examples of unscrupulous doctors prescribing medications with abuse potential in a profit-seeking manner. The current PM programs have allowed this illegal activity to continue, often for years before the trend is detected, due to the slow dissemination of information to the central database.

Patients currently steal prescription pads or forge legitimately obtained prescriptions. Current PM programs are unable to detect this illegal activity.

It is known in the art to provide packages, containers, dispensers, and the like which have provisions for dispensing individual doses of medication and have audible reminders of dosing times. Such a device is described in, for example, U.S. Pat. No. 4,617,557. It is also known to obtain and provide compliance data to prescribing physicians for review, as described in, for example, U.S. Pat. No. 6,198,383. However, it is not known to address the aforementioned issues that allow abuse, addiction and diversion of prescription medications to illicit use. Additionally, such medication packages may not sufficient incorporate child-resistant features. Furthermore, in regard to the patent referenced above which addresses compliance issues, the device described therein employs conductive traces that must be broken to detect removal of the medication from the package. This can result in decreased battery life of the medication package, and an increased number of required inputs to the central processing unit (CPU) in the medication package, thereby increasing the packaging cost.

Accordingly, there is a need for a medication packaging system which has improved packaging, including child resistant features and longer battery life, and which further incorporates both anti-diversion capabilities and compliance monitoring functions.

SUMMARY

According to the invention, a medication package medication package and associated system are provided to enable compliance and anti-diversion features. The medication package can have child resistant features and an electronic circuit board, having lower power requirements, which enables the compliance and anti-diversion capabilities. The data collected by the medication package can enable methods for addressing compliance and diversion issues wherein the compliance and anti-diversion capabilities of the medication package can be provided by a central processing unit ("CPU") contained in the medication package. The CPU can identify and record dose removal events and the medication package can further include components for conveying data of such events to other devices electronically via various mediums, including wired or wireless output. The data can be transferred to other computers or printed out. The data can be provided to various personnel involved in addressing the compliance and/or anti-diversion activities.

The medication package can comprise an array of doses contained in a blister pack, for example, a plastic bubble film defining a plurality of bubble chambers and a frangible layer covering the bubble chambers to retain the doses therein. The medication package can incorporate conductive traces associated with the frangible layer, and particularly where the opening into each bubble chamber (wherein a dose is contained) is covered by the frangible layer. Consequently, removal of a dose cannot occur without breaking the frangible layer and associated conductive traces, thus causing a detectable event. The CPU detects removal events when a dose is removed, and records the relative time of each removal.

The medication package can include a child proof cover, i.e., a cover resistant to access by children, and a heavy backing material and/or circuit board spacers on either side of the blister pack. The openings on the child proof cover do not align with the openings in the thicker backing material until the child proof cover is moved to a second, aligned position. The child proof cover cannot be moved to the aligned position without negotiating cooperating engagement features associated with the child proof cover, and at least the outer packaging material.

Initially, the blister pack can be loaded with medication by a licensed pharmacist and then assembled together with the thicker backing material, electronic circuit board portion, and other parts of the medication package, which are within the child resistant cover. The medication package can be manufactured in such a fashion that allows a pharmacist to "load" the blister pack with any combination or doses of pills, thereby providing dosing flexibility to the prescribing physician. The dose time interval can be preset when the dose package is assembled by the pharmacist.

The anti-diversion capability can further include providing a conductive trace incorporated into the periphery of the package such that removing a dose cannot be done without disturbing one of the breakaway conductive traces and causing a detectable event. Attempts to remove doses in an unconventional manner, to avoid breaking the frangible layer directly adjacent a bubble chamber, are thereby deterred. Also, the heavy backing material can be designed to cooperate with the blister pack in such a fashion that each dose must be removed from it in the prescribed manner, i.e., by pushing it through the frangible backing layer, or the removal of the dose will be detected and recorded by the CPU as a "tamper" event. The CPU can periodically check the status of the conductive traces to detect dose removal and tamper events.

The removal of the first dose can initiate the countdown timer sequence which in turn can trigger a visual or audible alarm when the next dose is to be taken by the patient. When each subsequent dose is removed from the package, the CPU can record the time elapsed from the previous dose, and can reset the timer to count down to the next dose. The CPU can also contain a unique and sequentially programmed package identifier code.

The CPU can transfer stored data to other devices, including a central database, via wired or wireless communication, including via the Internet, where the information can be processed and analyzed. This data may include information identifying the individual dose package code, patient compliance data and data reflecting the integrity of the medication package, as well as manually entered data, such as via a connected computer, reflecting the unique prescribing physician identifier data and unique patient identifier data. The collected data can be accessed and processed by various entities involved in implementing compliance and anti-diversion objectives.

BRIEF DESCRIPTION OF THE DRAWING FIGURES

FIGS. 3b and 3c are a mechanical details of a perforated opening in FIG. 3a.

FIG. 4 is a section view of the medication package in FIG. 3a.

FIG. 7a is a laid open front view of an embodiment of a circuit board configuration having both tamper proof traces and dose removal traces.

FIG. 7b is a mechanical detail of a perforated opening in FIG. 7a.

FIG. 7c is an electronic detail of a perforated opening in FIG. 7a.

FIG. 8a is a laid open front view of an embodiment of a circuit board configuration having only dose removal traces.

FIG. 8b is a mechanical detail of a perforated opening in FIG. 8a.

FIG. 8c is an electronic detail of a perforated opening in FIG. 8a.

DETAILED DESCRIPTION

Figure 1:
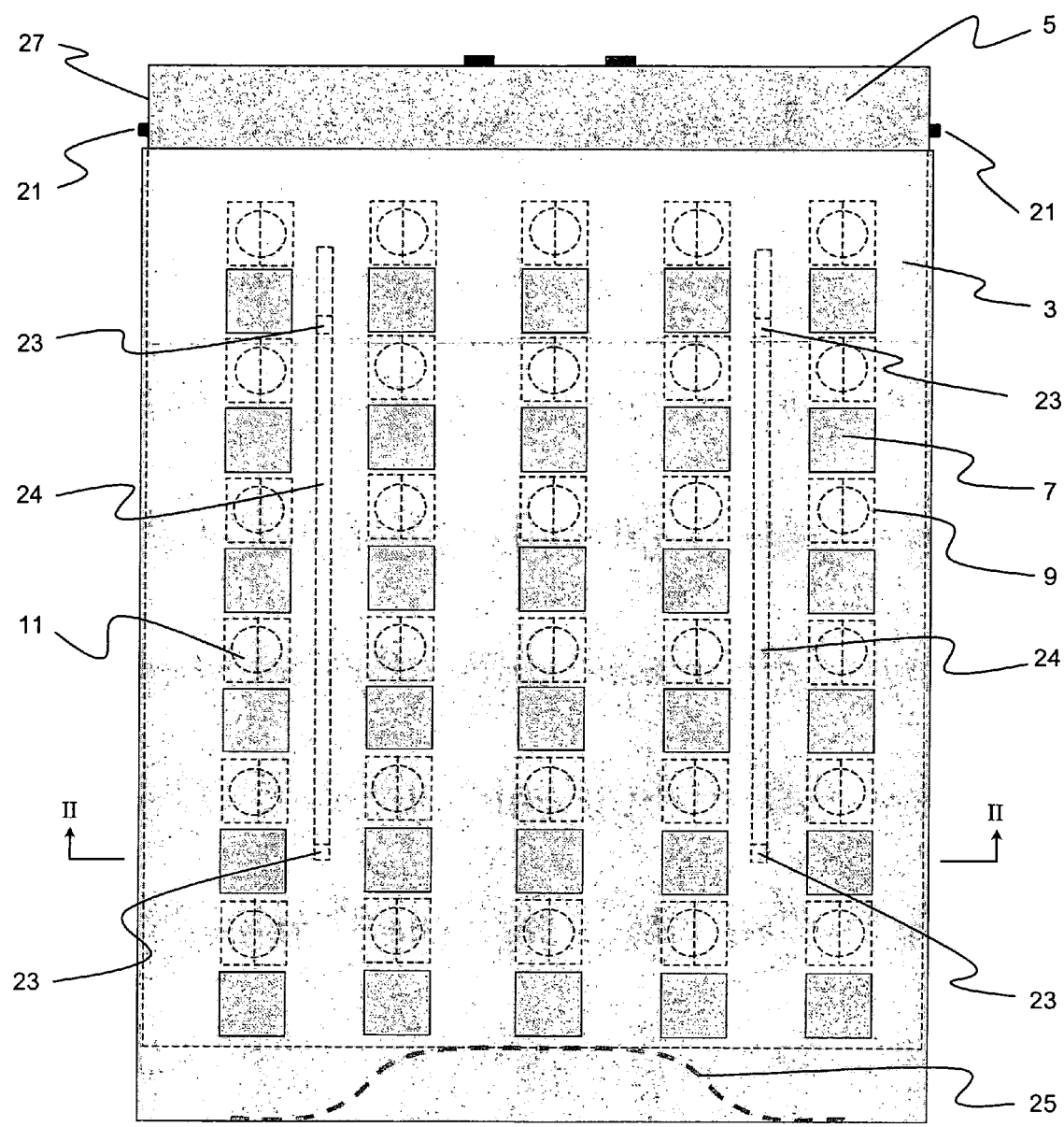
FIG. 1 is a front view of an embodiment of a medication package according to the invention.
Figure 2:
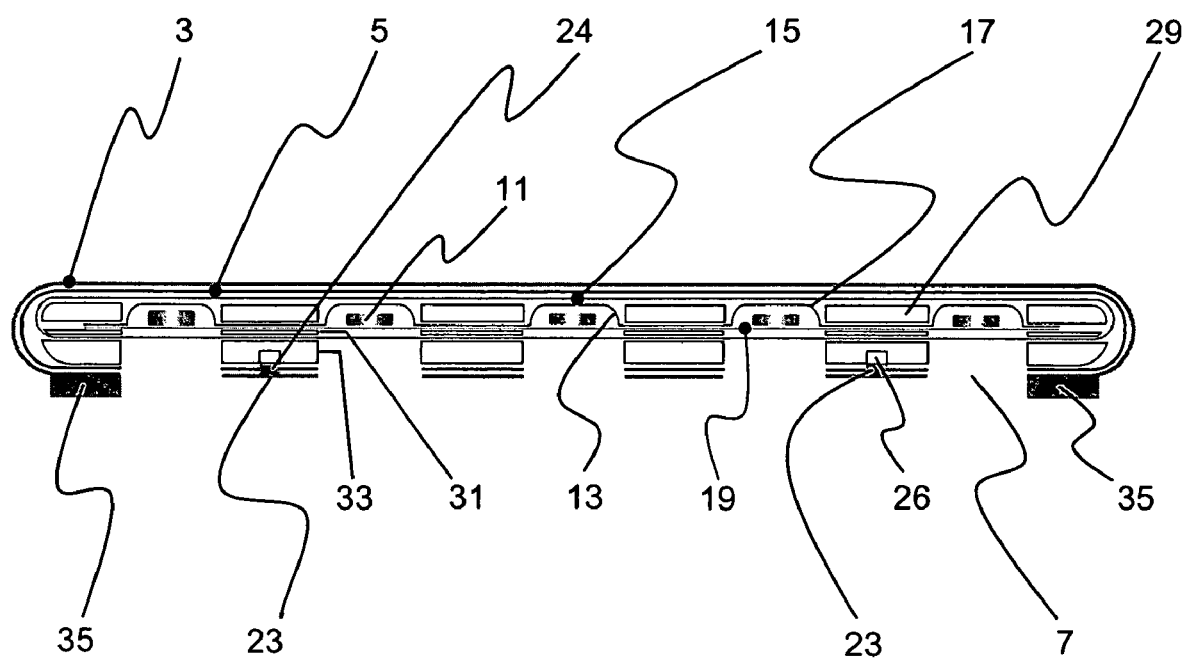
FIG. 2 is a view partially in section of the of the medication package in FIG. 1.

Referring now to FIGS. 1 and 2, there is shown a frontal view of an embodiment of a complete medication package 1 according to the invention, as configured for a 30-dose prescription, including a child proof cover 3 enveloping the outer packaging material 5 of the medication package 1. The child proof cover 3 can include multiple openings 7 arranged in rows and columns. When the child proof cover 3 is moved to a second position, these openings 7 are arranged to align with multiple perforated and/or scored regions 9, referred to hereinafter as perforated openings 9, in the outer packaging material 5 which are likewise arranged in rows and columns. Ultimately, these rows and columns of openings 7 and perforated openings 9 align with individual doses 11 of medication contained in a blister pack 13 (FIG. 2) enclosed within the outer packaging material 5. However, the child proof cover 3 cannot be moved to the second, aligned position unless multiple child resistant safety features are first negotiated.

As shown best in FIG. 2, the outer packaging material 5 encloses an electronic circuit board portion 15, and that the electronic circuit board portion 15 further surrounds the blister pack 13 formed of a plastic layer having formed therein a plurality of individually formed blisters 17, hereinafter referred to as bubble chambers 17, in which can be contained the individual doses 11 of medication. The other side of the blister pack can be covered by a frangible layer 19. Between the blister pack 13 and an upper side of the electronic circuit board portion 15 can be provided a layer of heavy backing material 29, and the lower side of the electronic circuit board portion 15 can be sandwiched between thin and thick circuit board spacers 33. The thin spacer 31 can be intermediate the blister pack 13 and the lower side of the electronic circuit board portion 15, whereas the thick spacer 33 can be opposite the thin spacer 31, but beneath the lower side of the electronic circuit board portion 15, such that the electronic circuit board portion 15 is sandwiched between the thin 31 and thick 33 spacers.

The rear face (not shown) of the child proof cover 3 can also have multiple openings, which can also be denoted by reference number 7, and which are also aligned with the openings 7 in the front face. "Feet" 35 can be provided on the child proof cover 3, which extend downwards from the rear face of the cover 3, and which can support the medication package 1 up off of an underlying surface (not shown), such as a table or counter top. As implied by the name, the "child proof" cover 3 can be provided with the aforementioned safety features that make the cover resistant to being manipulated by children. These safety features can include a pair of locking portions, such as safety push buttons 21, which can project from opposite the sides, or edges, of the outer packaging material 5, a cover closure spring 25, and slide tabs 23, which could also be rails, on the child proof cover 3 that cooperate with slots 24 in the outer packaging material 5. The safety pushbuttons 21 can prevent movement of the child proof cover 3 relative to the outer packaging material 5 unless the push buttons 21 are depressed to unlock the child proof cover 3 and permit movement to a position where the openings 7 are aligned with the doses 11 in the blister pack 13. The cover closure spring 25 urges the child proof cover 3 in a closed position in which the openings 7 are not aligned with the doses 11 in the blister pack 13. The child proof 3 cover must be pushed in against the closure spring 25 to compress the closure spring 25, and the closure spring 25 must be held in the compressed state in order to maintain the child proof cover 3 in the aligned position until the dose 11 is removed from the blister pack 13.

The slide tabs 23 are slidably received in the slots 24, and a cover closure spring 25 can be provided to urge the child proof cover 3 in a normally unaligned position. In cooperation with the child proof cover 3 safety features, a portion of the enclosed medication package 1 extends from within the surrounding child proof cover 3, i.e., the child proof cover 3 can have a length somewhat shorter than the enclosed portion of the medication package 1. The portion 27 of the outer packaging material 5 of the medication package 1 which extends out beyond the child proof cover 3 can have the aforesaid safety push buttons 21 which must be negotiated in order to permit the child proof cover 3 to slide relative to the enclosed medication package 1, via the cooperating slide tabs 23 and slots 24, in order to move the child proof cover 3 to the second position with the openings 7 aligned with the doses 11 contained in the enclosed blister pack 13. The safety push buttons 21 can retractably project outwards from the sides of the outer packaging material 5 such that the openings 7 in the child proof cover 3 cannot align with the perforated openings 9 in the outer packaging material 5, and thus the individual doses 11 in the enclosed blister pack 13.

The child proof cover 3 and closure spring 25 can be designed such that depressing the safety push buttons 21 permits the enclosed portion of the medication package 1 to be pressed into the child proof cover 3, by compressing the closure spring 25, to align the openings 7 in the child proof cover 3 with the perforated openings 9 in the outer packaging material 5 and the individual doses 11 contained in the enclosed blister pack 13. As shown, the slide tabs 23 on the inside of the rear face of the child proof cover 3 can project inwardly toward the outer packaging material 5, and the slots 24 can be provided in the lower face of the outer packaging material 5 for slidably receiving the slide tabs 23. The slide tabs 23 and slots 24 can help position and maintain the child proof cover 3 in a properly aligned sliding relationship to ensure alignment of the openings 7 in the child proof cover 3 with the doses 11 stored in the enclosed blister pack 13 when the child proof cover 3 is negotiated.

Figure 9:
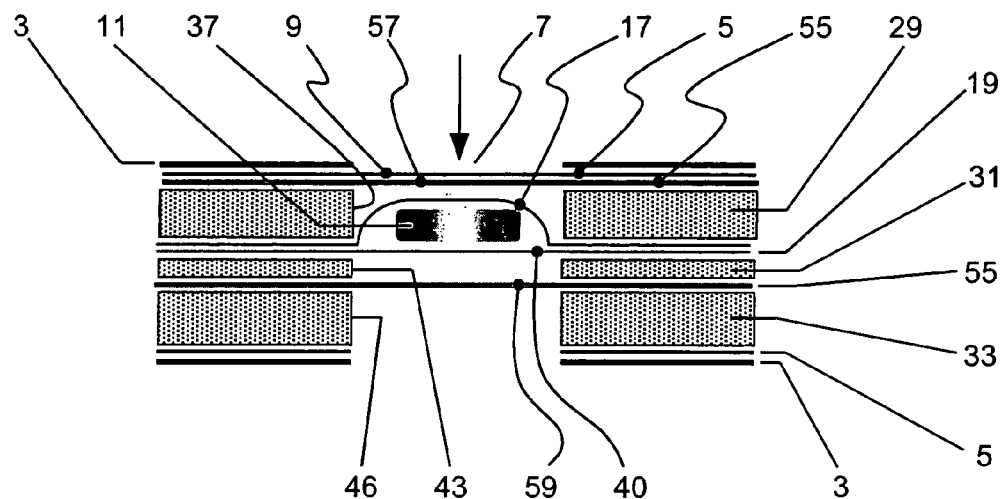
FIG. 9 is a detail view of FIG. 4a illustrating removal of a dose of medication.
Figure 9:
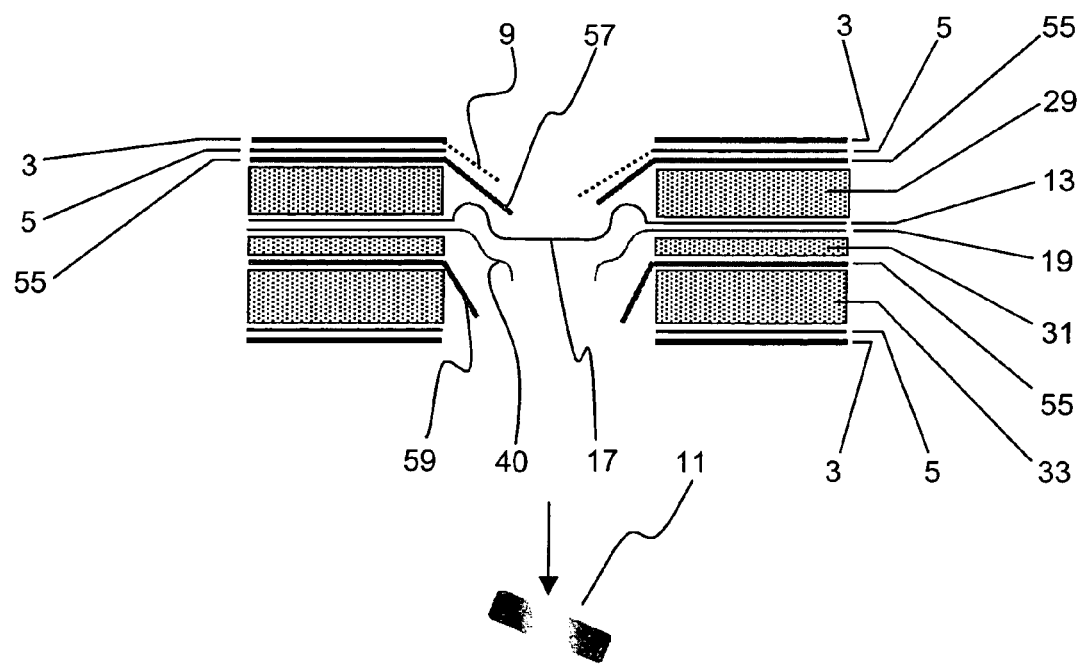

The child proof cover 3 must be moved to a position at which the openings therein align with the perforated openings 9 in the outer packaging material 5 and thus the individual doses 11 of medication contained in the blister pack 13, before it is possible to remove any doses 11. Generally, opening the fully assembled medication package 1 and removing a dose 11 of medication can be accomplished by a three step sequence: depressing each safety push button 21; sliding the medication package 1 relative to the child proof cover 3 to align the openings 7 therein with the perforated openings 9 in the outer packaging material 5; and pressing through the openings 7 and perforated openings 9 to dislodge a dose 11 from the enclosed blister pack 13 and out from the package 1. Removal of a dose 11 can most easily be done by placing the medication package 1 on a flat surface prior to pressing through the openings 7 to dislodge the dose 11 from the blister pack 13. Additional details of the pill removal procedure will be described hereinafter, and especially in connection FIG. 9.

Figure 3A:
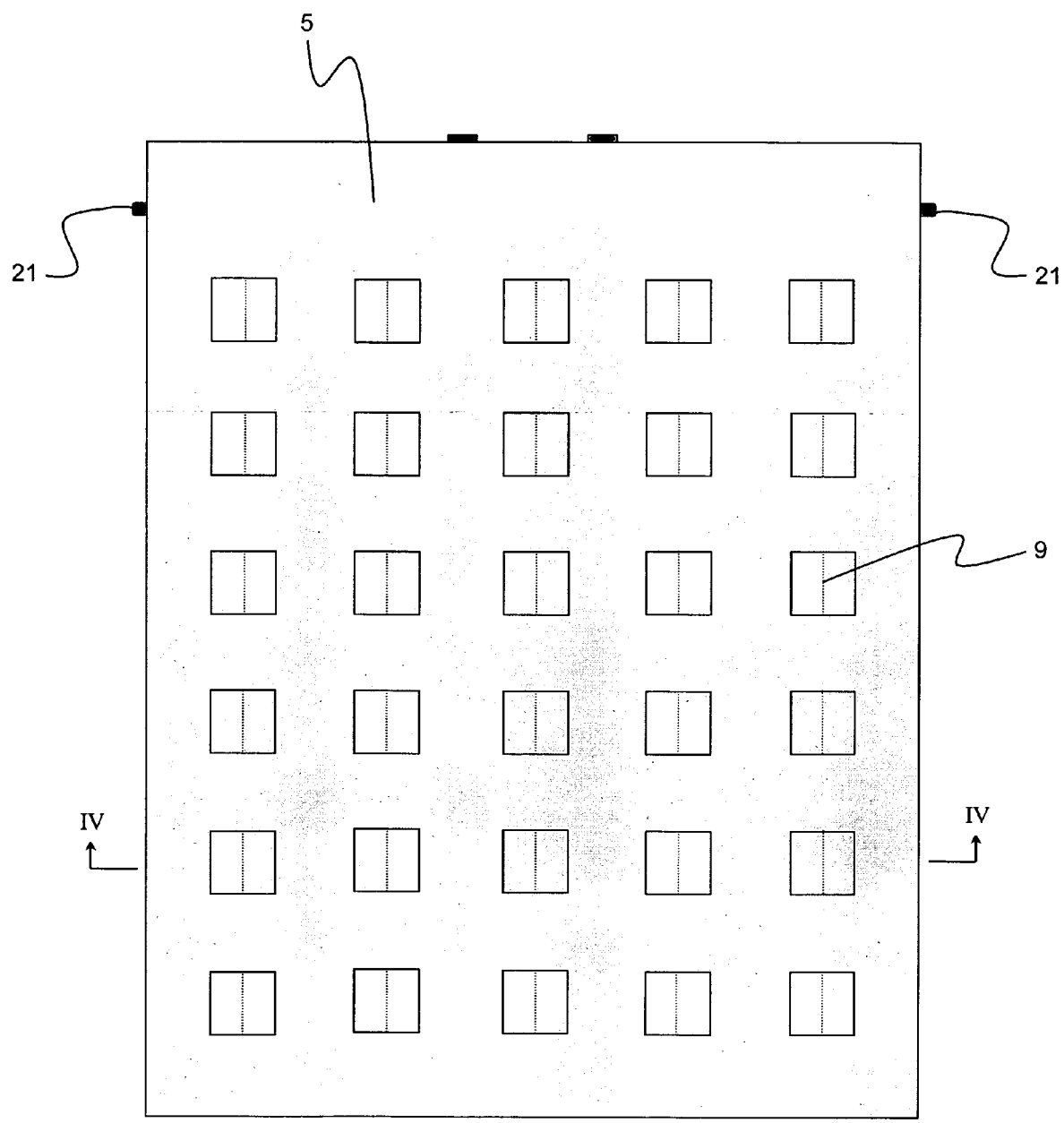
FIG. 3a is a front view the medication package shown in FIG. 1 with a childproof cover portion removed.
Figure 3B:
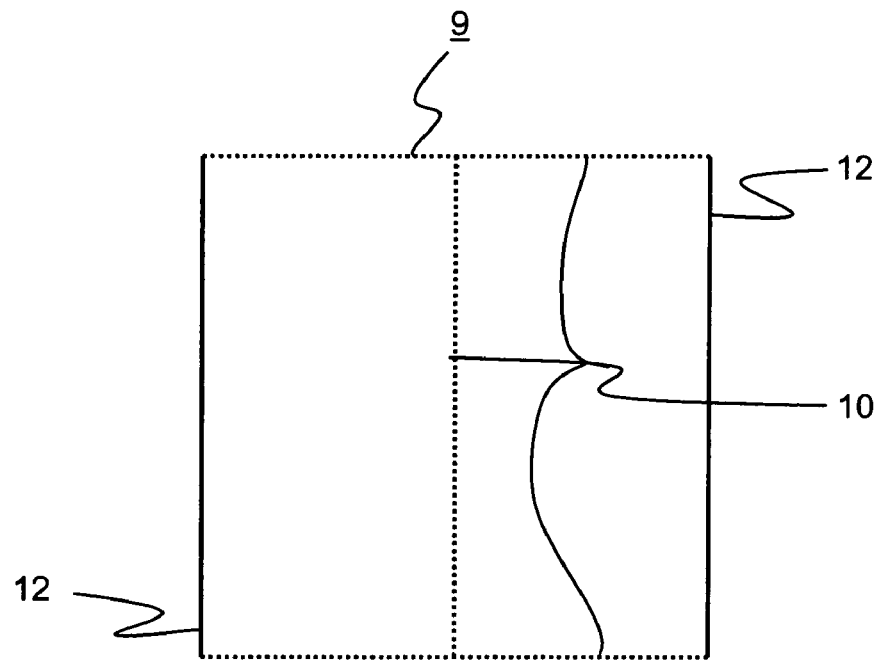
Figure 3C:
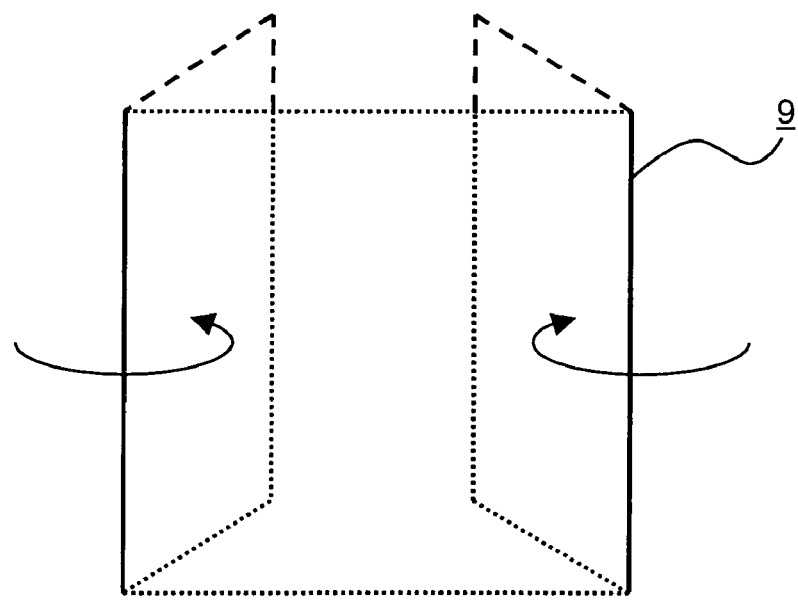
Figure 4:
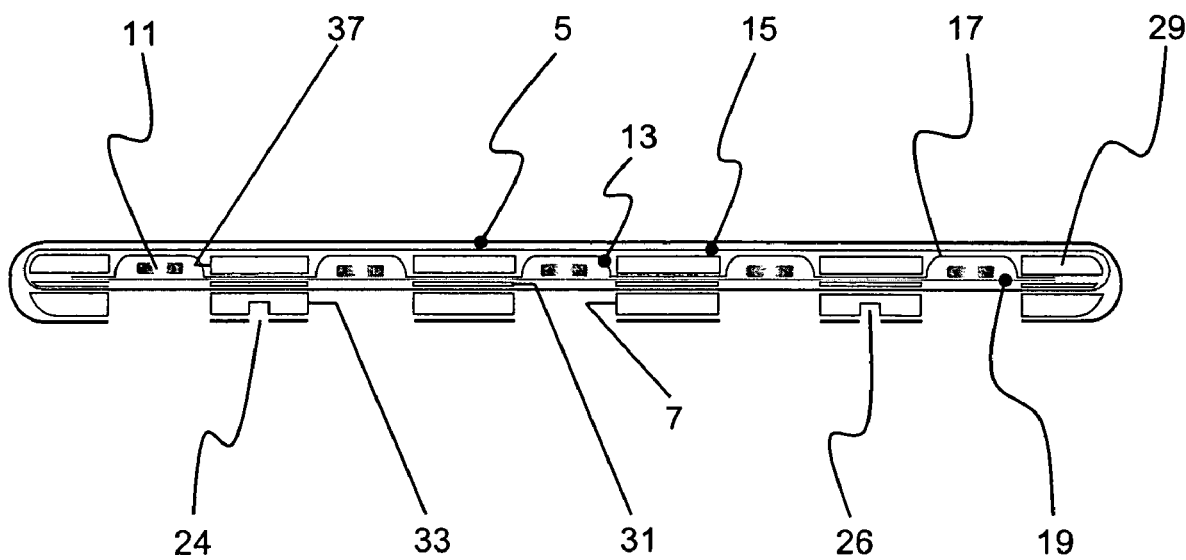

Referring now to FIGS. 3a through 4, further details of the portions of the medication package 1 surrounded by the child proof cover 3 and the outer packaging material 5 can be viewed. As shown with the child proof cover 3 removed, the outer packaging material 5 can have the plurality of perforated openings 9 referred to above. A detail view of a perforated opening 9 is shown in FIGS. 3b and 3c, which show that the region can have scoring 12 at opposite sides and perforations 10 along the top, bottom, and centerline of the region. It is to be understood that these, or any other similar perforated openings of other portions of the medication package 1 as described hereinafter, could instead be true "openings." As shown in FIG. 3c, applying pressure, particularly against the perforated center line, will result in pushing through the opening 9 by tearing along the perforations 10 and folding, or hinging, about the scoring 12. The perforated openings 9 in the outer packaging material 5 are located for alignment with each of the individual doses 11 contained in the bubble chambers 17 in the enclosed blister pack 13.

The cross section view in FIG. 4 provides a more detailed look at the inner arrangement of the components of the medication package 1, showing that the outer packaging material 5 surrounds the electronic circuit board portion 15, and that the electronic circuit board portion 15 encloses the blister pack 13 containing the individual doses 11 of medication. Other layers of the assembly can also be provided, including a heavy (e.g., thicker or more rigid) backing material 29 adjacent the bubble chamber 17 side of the blister pack 13, intermediate the blister pack 13 and an upper side of the electronic circuit board portion 15. The heavy backing material 29 can have a plurality of openings 40 which are aligned with the raised bubble chambers 17 of the blister pack 13, such that the bubble chambers 17 project through the openings 40 in the heavy backing material 29, thus permitting the heavy backing material 29 to lie generally flat adjacent the blister pack 13. The thickness of the heavy backing material 29 can be generally equal to the depth of the bubble chambers 17, which accounts for the thickness of the raised bubble chambers 17, thus creating a generally flat surface to facilitate closely adjacent positioning of the upper side of the electronic circuit board portion 15 against the bubble chambers 17. The heavy backing material 29 can also be designed to cooperate with the blister pack 13 to prevent removal of a dose 11 of medication in an unconventional manner, i.e., in some manner other than forcing the dose 11 through the frangible layer 19 of the blister pack 13. Providing a generally flat surface can be desirable because the upper side of the electronic circuit board portion 15 has perforated openings with associated conductive traces provided thereon (described in connection with FIGS. 7a and 8a) adjacent each of the bubble chambers 17, which contain the individual doses 11 of medication. It can be desirable that the perforated openings and conductive traces be closely adjacent the bubble chambers 17 to facilitate both removal of a dose 11 and the detection of such a removal.

The blister pack 13, which is generally the innermost portion of the medication package 1, can comprise two layers. The first can be the blistered plastic layer 14 having formed therein the bubble chambers 17, in which are disposed the individual doses 11 of medication. The second layer is the frangible backing 19, which covers the open side of the bubble chambers 17. The frangible layer 19 can be a thin sheet of frangible material, which can also be made from a conductive material, such as a thin foil layer. The frangible foil layer 19 can have perforated openings 40 adjacent each of the bubble chambers 17 to facilitate removal of the doses 11 of medication therethrough. Adjacent the frangible layer 19 of the blister pack 13, intermediate the frangible layer 19 and the upper side of the electronic circuit board portion 15, can be provided a further layer of material, referred to previously as the thin circuit board spacer 31, or simply a thin spacer 31. The thin circuit board spacer 31 can, like the heavy backing material 29, also be provided with a plurality of openings 43 therethrough, each of which can be located to align with all of the following: the perforated openings 40 in the adjacent frangible layer 19 of the blister pack 13; the bubble chambers 17 covered thereby; the openings in the heavy backing material 29; and perforated openings in the upper side of the electronic circuit board portion 15. A second spacer referred to previously as the thick circuit board spacer 33, or simply a thick spacer 33, can also be provided, and can be positioned beneath of the lower side of the electronic circuit board portion 15. Thus, the lower side of the electronic circuit board portion 15 is sandwiched between the thin 31 and thick 33 circuit board spacers. As with the upper side of the electronic circuit board portion 15, the lower side thereof can likewise have a plurality of perforated openings, which are position in alignment with the perforated openings in the upper side thereof. Similarly to the thin spacer 31, the thick spacer 33 can have a plurality of openings 46, which can be located to align with each of the perforated openings in both sides of the electronic circuit board portion 15, the openings 43 in the thin spacer 31, the perforated openings 40 in the frangible layer, and the bubble chambers 17. As shown, the thick circuit board spacer 33 is intermediate the lower side of the electronic circuit board portion 15 and the rear face of the outer packaging material 5. The thick spacer 33 can also have slots 26 in the underside thereof which align with the slots 24 (see FIGS. 2 and 4) in the rear face of the outer packaging material 5, such that the slide tabs 23 on the lower face of the child proof cover 3 can extend through the outer packaging material 5 and be slidably received in the slots 24 in the thick spacer 33.

Figure 5:
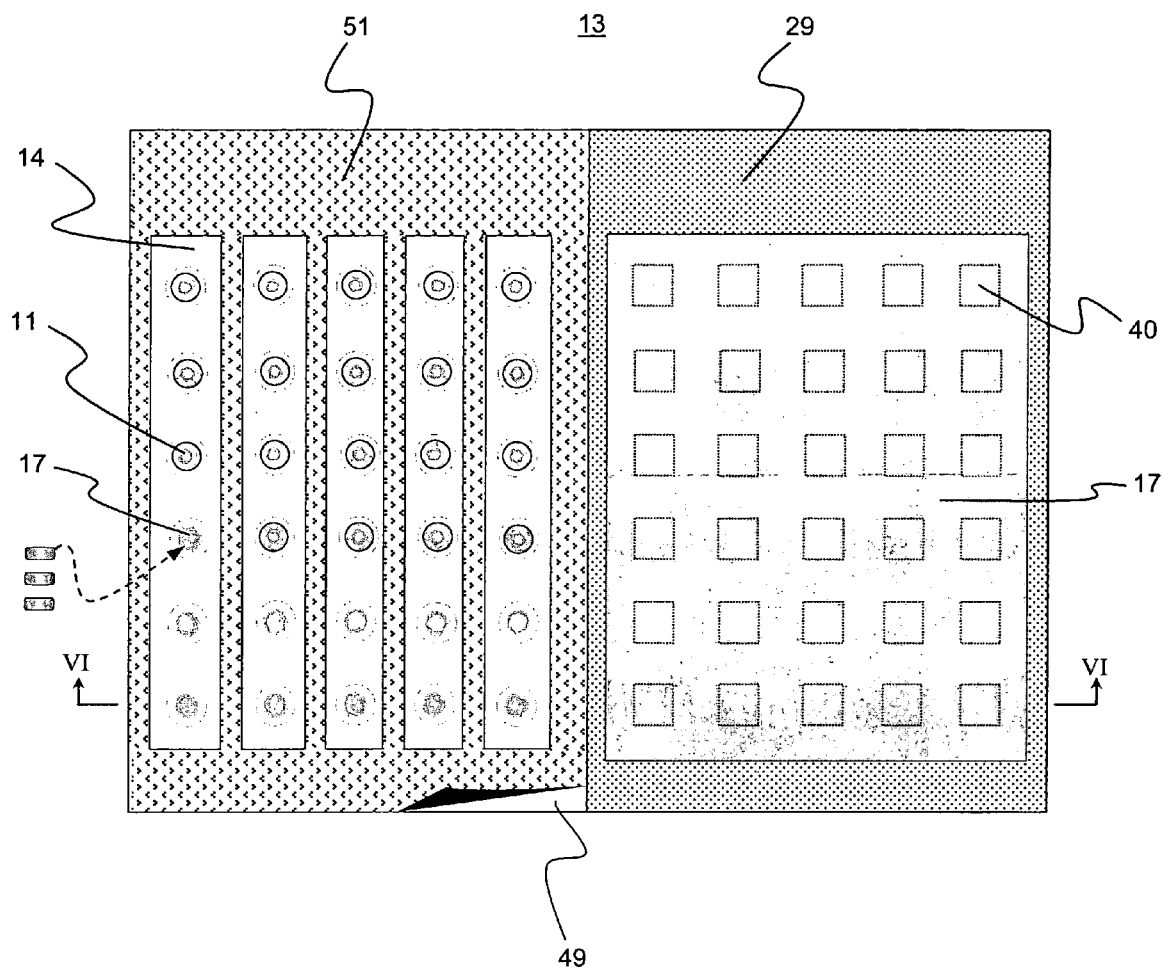
FIG. 5 is a laid open view of a medication package as shown in FIG. 1.

Referring to FIG. 5, prior to assembly the medication package 1 is initially open, much like an open book, such that the doses 11 can be loaded into the blister pack 13 by the pharmacist. The various layers are best viewed in FIG. 6. The blister pack 13 is initially open, i.e., the frangible layer 19 has not yet been adhered to the plastic blister layer 14 so that the medication can be inserted into each bubble chamber 17 prior to assembly of the filled blister pack 13. The doses 11 are loaded into the individual bubble chambers 17, as shown on the left side of the figure. The plastic blister layer 14 can also include an adhesive backing 49 with a protective cover 51 on the flat surfaces of the bubble layer intermediate the bubble chambers 17. After the doses 11 of medication are loaded into the bubble chambers 17, the protective layer 51 is removed, exposing the adhesive layer 49. The right side of the blister pack 13 can then be folded over onto the left side and, by applying pressure thereto, adhered together via the adhesive layer 51 thus forming a completed, sealed blister pack 13.

Figure 6:
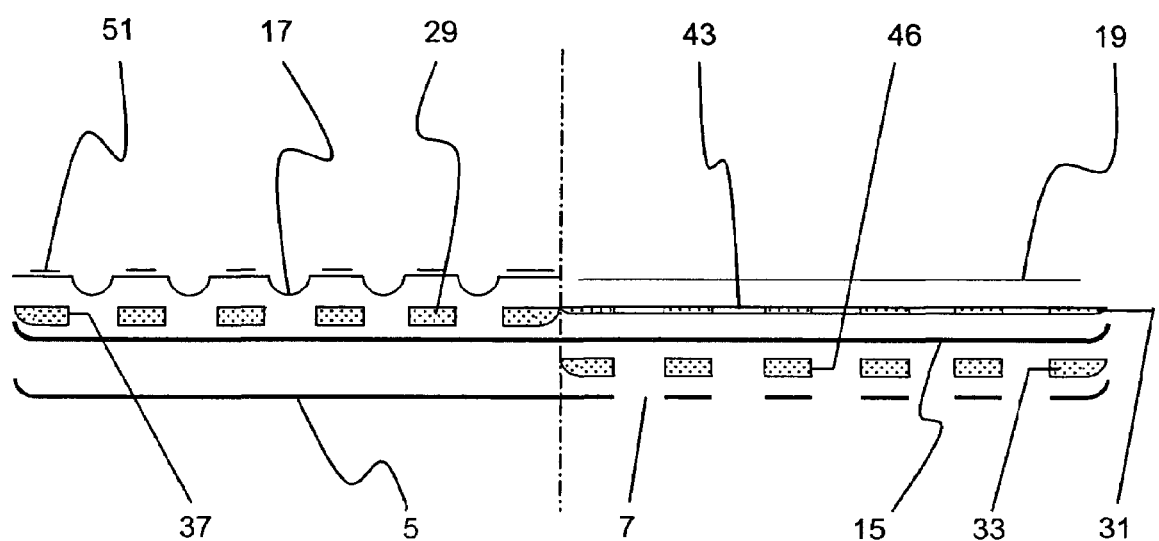
FIG. 6 is an exploded partial section view of FIG. 5.

The left side of the blister pack 13 shows the frangible backing 19 material that covers the openings into the bubble chambers 17. The frangible backing material 19 can have the aforementioned perforated openings 43 where it covers each of the bubble chambers 17. However, if the layer 19 is sufficiently frangible, perforations or scoring would not be necessarily required. Preferably, the frangible material is a conductive foil layer. As best shown in FIG. 6, the left side of the blister pack 13 (i.e., the upper half of the completed, "folded over" medication package 1) will be associated with the thicker heavy backing material 29 and the right side (i.e., the lower half of the completed medication package 1) will include the thin circuit board spacer 31 and a thick circuit board spacer 33. The electronic circuit board portion is thus sandwiched between the thin 31 and thick 33 spacers. When the doses 11 of medication are loaded into the blister pack 13, and the entire assembly of layers is "folded over" by closing the halves against each other, the structure obtained will be as just described in FIG. 4.

Generally, the upper and lower (or left and right) "halves" or portions can be brought over adjacent each other by folding along a centerline. However, such as in the case of the electronic circuit board portion 15 in particular, the two halves, or sides, of some layers, particularly the electronic circuit board portion 15, can be radiused to bring the two side into a folded over relationship. This can be done to avoid potential damage to the conductive traces on the electronic circuit board portion 15 which could be cause by simply "folding" the electronic circuit board portion 15 about a centerline. Alternatively, the left and right side portions of the laid open medication package can be entirely separate halves which are secured over against each other in a manner to hold the layers together as depicted, for example, in FIG. 4.

Figures 7A, 7B, 7C:
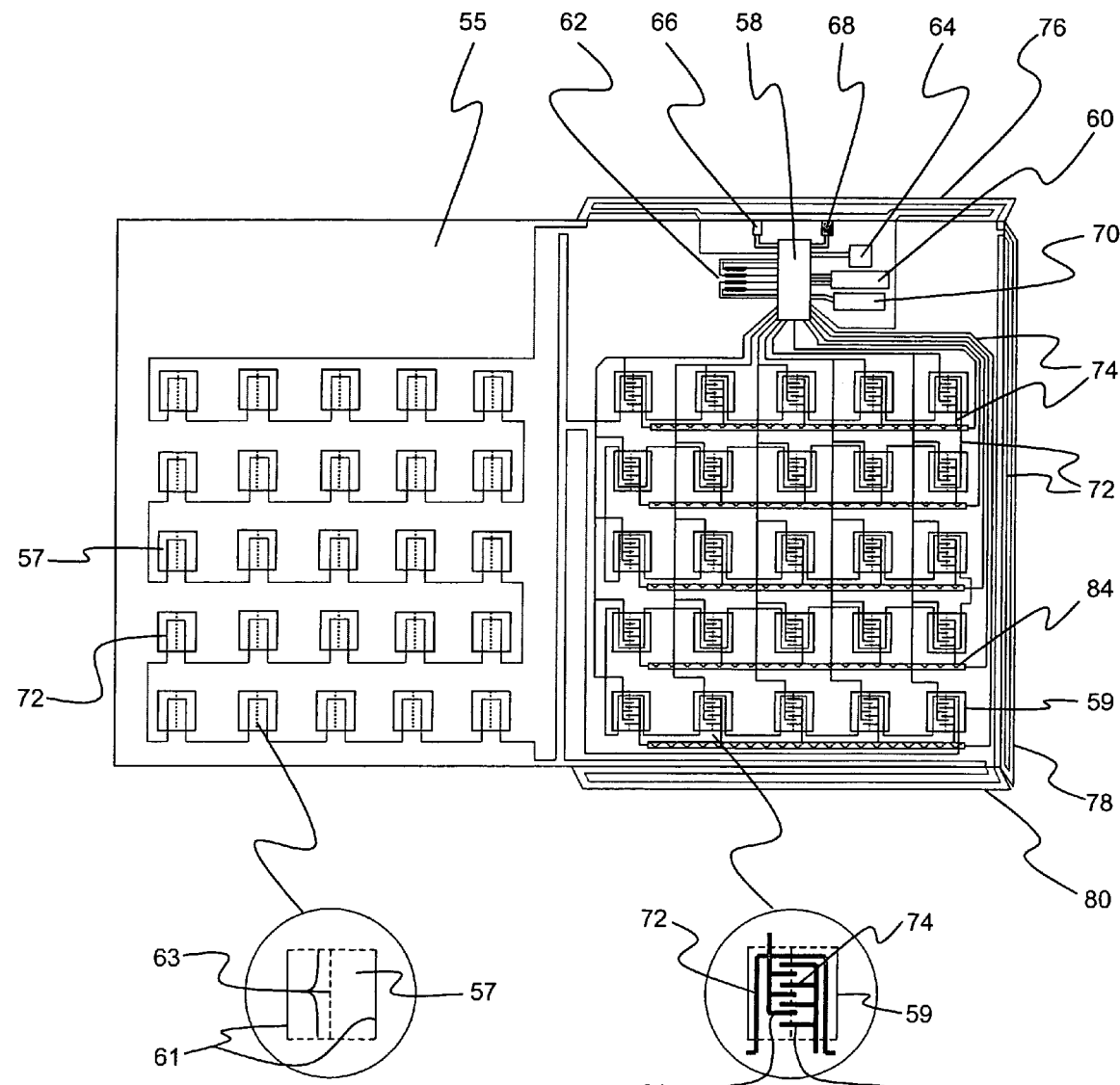

Referring now to FIG. 7a, a flat, laid open, view of a particular embodiment of an electronic circuit board portion 55 is shown. As described previously, when "folded over," the electronic circuit board portion 55 will enclose the blister pack 13, in a manner wherein the left (upper) side of the electronic circuit board portion 55 will be adjacent the bubble chambers 17, and the right (lower) side thereof will be separated from the frangible layer 19 of the blister pack 13 only by the thin circuit board spacer 31. Both the upper and lower sides of the electronic circuit board portion 15 have a plurality of perforated openings 57 and 59, respectively, with each perforated opening 57, 59 located to align with the bubble chambers 17, and thus also with the perforated openings 40 on the frangible layer 19, as well as each of the openings 37, 43, 46 in each of the heavy backing material 29 and thin 31 and thick 33 circuit board spacers.

The electronic circuit board portion 55 can have appropriate electronic components mounted thereon, as shown at the top right side thereof, which can include, for example, the CPU 58 (assumed to include memory elements), a battery 60, a clock generator, or timer 62, a sound generator 64 (for providing an audible alarm), a data output/input port 66, an LED 68 (for providing a visual alarm), and an EEPROM 70. Additional components can also be included, as may be found useful in carrying out the electronic functions of the medication package 1.

The perforated openings 57, 59 on each side of the electronic circuit board portion 55 can be as shown in the mechanical opening detail view in FIG. 7b, which can have scoring at opposite sides and perforations along the top, bottom and center thereof The perforated openings 57, 59 can thus open in the same manner as shown in FIG. 3c. This embodiment of the electronic circuit board portion 55 can be provided with two types of conductive traces and the requisite electronic components for effecting both anti-diversion and compliance functions. As shown, the left side of the electronic circuit board portion 55 includes the perforated openings 57 which positioned to lie adjacently above each bubble chamber 17 of the blister pack 13. Conductive anti-tamper traces 72 can be provided associated with each of the perforated openings 57, 59 on each side of the electronic circuit board 55 to effect the anti-diversion function. The right side of the electronic circuit board 55 includes the perforated openings 59 which are positioned to lie below the bubble chambers 17, adjacent the perforated openings 40 on the frangible conductive foil layer 19. Conductive dose removal traces 74 are provided associated with each of these perforated openings 59 to detect dose removals. The embodiment shown includes both types of conductive traces for a 25-dose blister pack 13. As shown, tamper proof traces 72 can be provided on each of the perforated openings 57 and 59 on both left and right sides of the electronic circuit board portion 55. Additionally, the tamper proof traces 72 can be provided on peripheral side portions 76, 78, 80 which are designed to fold over the three otherwise exposed sides of the blister pack 13 when the medication package 1 is assembled by bringing the two halves together. The anti-tamper traces 72 can further be provided around the entire periphery of the medication package, i.e., side portion 75 in addition to side portions 76, 78 and 80 to detect any attempts to remove doses 11 in an unconventional manner.

The circuit board can be made of a flexible substrate and, as illustrated, exhibits one possible arrangement of electronic components and conductive traces 72, 74. In the embodiment of the electronic circuit board 55 shown, the tamper proof traces 72 (shown in lighter lines) could be provided on the back surface of the electronic circuit board portion 55, and the dose removal traces 74 (shown in darker lines) could be provided on the front surface thereof, closely adjacent the conductive foil layer 19 of the blister pack 13. Insulating strips 84 can be provided where necessary to prevent short circuits between overlapping portions of the conductive dose removal traces 74. Alternatively, if both the tamper proof 72 and dose removal 74 traces are placed on the same surface of the electronic circuit board portion 55, additional insulating strips, such as insulating strips 84, can be utilized to prevent short circuits between overlapping portions of the traces. Detailed mechanical and electronic views of the perforated openings 57, 59 are shown in FIGS. 7b and 7c.

The embodiment of the electronic circuit board portion 55 contemplates a circuit design with overlapping conductive dose removal traces 74, using the aforesaid strips of insulating material 84 interposed at overlapping locations. As shown, five horizontal traces (underneath the insulating strips 84) between rows of perforated openings 59 can be used in sequence to supply a voltage, and five vertical traces between the columns of perforated openings 59, can be used synchronously to sense voltage. In this manner, a momentary continuity between dose removal traces 74, as will result from a dose 11 removal, can be checked individually for every one of the 25 positions using only ten lines. For example, if "N" lines are used to supply voltage and "M" lines are used to sense voltage, then N×M positions can be tested using only N+M lines. This arrangement can require that voltage and sense traces cross each other. Therefore, an appropriate manufacturing sequence would be to first print all the voltage traces (or sense traces), print the insulating strips 84 to cover all expected crossing points, then lastly print all the sense traces (or voltage traces).

The anti-diversion, or tamper proof conductive traces 74 can be designed such that pushing on the bubble chamber 17 to remove a dose 11, via the various openings and perforated openings in the medication package 1, will break the perforated opening 57 above the dose 11, and the associated tamper proof trace 72 thereon, which event will be detected by the CPU 58. Similarly, when a dose 11 is forced from the bubble chamber by such pushing action, the conductive foil layer 19 will be ruptured, and will contact an associated dose removal trace 74 on the perforated opening 59, resulting in a continuity event which will be detected by the CPU 58.

In the case of the tamper proof traces 74, a voltage is normally applied to the traces, and thus breaking the trace 72 on any particular perforated opening 57 will thus result in an open circuit that is sensed by the CPU 58. In contrast, as best understood from the electronic detail view in FIG. 7c, the dose removal traces 74 can actually be a pair of two separate traces 81 and 82. The pair of traces 81, 82 can be electrically discontinuous, i.e., not normally in contact with each other.

However, when the conductive foil layer 19 is ruptured by a dose 11 removal, the conductive foil 19 will contact the perforated opening 59, and concurrently contact each of the pair of traces 81, 82, thereby creating a continuity therebetween which will be sensed by the CPU 58 and identified with the specific perforated opening 59, and associated dose 11 of medication.

As discussed above, two types of events are designed to be detected utilizing the two types of conductive traces. One event is a "broken trace" and the other is a "continuity."

The tamper proof traces 72 can be one continuous trace associated with each perforated opening 57, 59 and can further surround a periphery of the medication package 1. If an attempt is made to cut through the sides of the package 1 to remove a dose 11 from the blister pack 13 unconventionally, a break in the tamper proof trace 74 will be detected by the CPU 58 as a "tamper" event. As a power savings consideration, the tamper proof trace 72 is not designed as "normally open" due to its length and extensive coverage of the entire package 1. The battery 60 drain from this one trace is negligible. Since the tamper proof trace 72 one continuous trace, the only the initial break will be detected by the CPU 58. The tamper proof trace 72 can be particularly useful for detecting, and inhibiting, diversion of medication at a pharmacy.

In contrast, the dose removal traces 74 are "normally open" traces provided on the perforated opening of the electronic circuit board portion 15 which underlie the individual dose locations in the blister pack 13. As described above in connection with FIG. 7c, there is no continuity between the pair of separate traces 81, 82 until a dose 11 is removed and the conductive foil 19 causes a brief connection therebetween. An advantage of this design is that the battery 60 will be not drained by having the CPU 58 continuously interrogating dose 11 locations before the first dose 11 is even removed. Instead, the removal of the first dose of medication can be the signal to initiate the timer 62.

The portion of the CPU 58, i.e., the particular pin, which monitors the tamper proof trace 72 will read a voltage (i.e., a '1') in the normal state, and no voltage (i.e., a '0') when the package 1 is physically tampered with as to result in a broken tamper proof trace 72. A continuity detection by the CPU 58 signals the removal of a dose 11 in the prescribed manner. In contrast to the tamper proof traces 72, the dose removal conductive traces 74 associated with each of the perforated openings 59 have no continuity in the normal state. Thusly, before a first dose 11 is removed from the blister pack 13, the individual CPU 58 pins monitoring the respective perforated openings 59 will register no voltage. However, when a dose 11 of medication is pushed through frangible conductive foil layer 19, the foil 19 will cause a continuity between the pair of separate traces 81, 82. This continuity results in a voltage "spike" at the associated pin of the CPU 58. After the dose 11 is entirely removed from the package 1, the dose removal trace 74 associated with the particular perforated opening 59 is designed to be sheared off in order to prevent an erroneous repeat signal at that location.

At such time as the CPU 58 detects a continuity, the preceding break in the tamper proof trace 72 will not be recorded as a tamper event. However, this can be conditional upon removal of the dose 11 being recorded by the CPU 58 within a predetermined time frame. The detection of the broken tamper proof trace 72 will not be recorded as a tamper event so long as the dose 11 is removed within the predetermined time frame. If the dose 11 is not removed within the preset time frame, the event will then be recorded as a tamper event. As explained above, only the initial break of the tamper proof trace 72 will be detected. Thus, the preceding condition will only exist in regard to the initial break of a tamper proof trace 72.

Each time a subsequent dose 11 is removed from the package 1 by the patient, the CPU 58 records the time elapsed from the previous dose 11, and resets the timer 62 to count down to the removal time for the next dose 11. Removal of the first dose 11 of medication, i.e., the voltage spike created thereby, can be used as the initiating event for the CPU 58 to activate the timer to begin recording time/counting down. After sensing this voltage spike, the CPU 58 will define the event as "time zero," the timer 62 will begin accumulating time. The elapsed time between dose removals can continually be compared with the preset dosing schedule. In this manner the CPU 58 can detect when the patient should take the next dose 11. The CPU 58 can, at the set time to remove the next dose 11, activate a visual alarm (via the LED 78) and/or audible alarm (via the sound generator 64) when the next dose 11 is due to be taken by the patient. When each subsequent dose 11 is removed from the package, the CPU 58 can record the time elapsed from the previous dose 11, and can reset the timer 62 to count down to the next dose 11. When the CPU 58 detects the next dose 11 should be removed, the LED 78 can be illuminated, or caused to blink, and/or the audible alarm can also be sounded. The visual and/or audible alarm can continue for a preset time if the dose 11 is not removed. The proper removal of the subsequent dose 11 causes the aforesaid voltage spike, that is sensed by the CPU 58, which can respond by silencing and the alarms and resetting the countdown timer 62.

The CPU 58 accumulates relative time from when the first dose 11 was removed, and not the actual time of day. This allows the preset dosing schedule to be automatically adjusted to the patient's daily schedule, for example, patients who work night shift will be taking doses at different times than ones who work during the day shift. The dose schedule can be set by the pharmacist when the medication package 1 is assembled by writing the pertinent data to EEPROM 70, for example via a modem associated with a personal computer used by the pharmacist. The package 1 can be designed such that without the necessary software, the dose schedule cannot be altered once established by the pharmacist.

The medication package 1 can include a battery 60, which can be part of the electronic circuit board portion 55. The battery 60 can be installed at the time the medication package is assembled. Since the CPU 58 remains essentially inactive, except for monitoring the tamper proof traces 72, the shelf life of the battery 60 can be about 5 years, well exceeding the shelf life of the medication.

Among other information, the CPU 58 can store a unique and sequentially programmed package identifier code. The CPU 58 can transfer stored data to other devices, including a central database, via wired or wireless communication, including via the Internet, where the information can be processed and analyzed. This data may contain information identifying the individual dose package code, patient compliance data, and data reflecting the integrity of the medication package 1, as well as manually entered data, such as via a connected computer, reflecting the unique prescribing physician identifier data and unique patient identifier data. The collected data can be accessed and processed by various entities involved in implementing the compliance and anti-diversion objectives.

The CPU 58 can control all the logic of the medication package 1, including using a clock generator to track elapsed time between doses, giving alarms via the LED 68 and/or sound generator 66, and responding to temporarily closed circuits, i.e., continuities, detected via the dose removal traces 74 as doses are removed.

According to the invention, CPU 58 logic could follow, for example, rules such as these:

1. If no dose 11 has yet been removed, monitor the tamper proof traces 72 continuously to ensure the package was not tampered with in an attempt to remove pills unconventionally.
2. When the first dose 11 is removed, the CPU 58 captures that event as time zero and activates the timer 62 to begin counting down time until the next preset scheduled dose removal.
3. If a dose 11 is removed before the countdown timer 62 reaches zero, the actual elapsed time since the last dose will be recorded, and the timer 62 will begin a new countdown.
   (a) If the actual time was no less than 80%, for example, of the prescribed time, the timer 62 will start at the prescribed delay plus the "leftover" time. In other words, the new target time will be the same as if the dose 11 had been removed exactly on schedule.
   (b) If the actual time was no more than 120%, for example, of the prescribed time, the timer 62 will start at the prescribed delay minus the "extra" time. In other words, the new target time will be the same as if the dose 11 had been removed exactly on schedule.
   (c) Otherwise, a "noncompliance" event will be recorded, and the timer will reset to the prescribed delay between doses, which probably will change the time of day when doses are scheduled.

Each CPU 58 in a medication package 1 can be programmed with a unique identifier code to enable its identification when the medication packaging is coupled with a central database collection site via its specified form of data transmission, such as an infrared data output port. When coupled with the compliance data collected as previously described, this data string will represent a unique set of information specific to each individual medication package 1. CPU 58 is connected to all of the components on the circuit board the tamper proof 72 and dose removal 74 conductive traces.

Figures 8A, 8B, 8C:
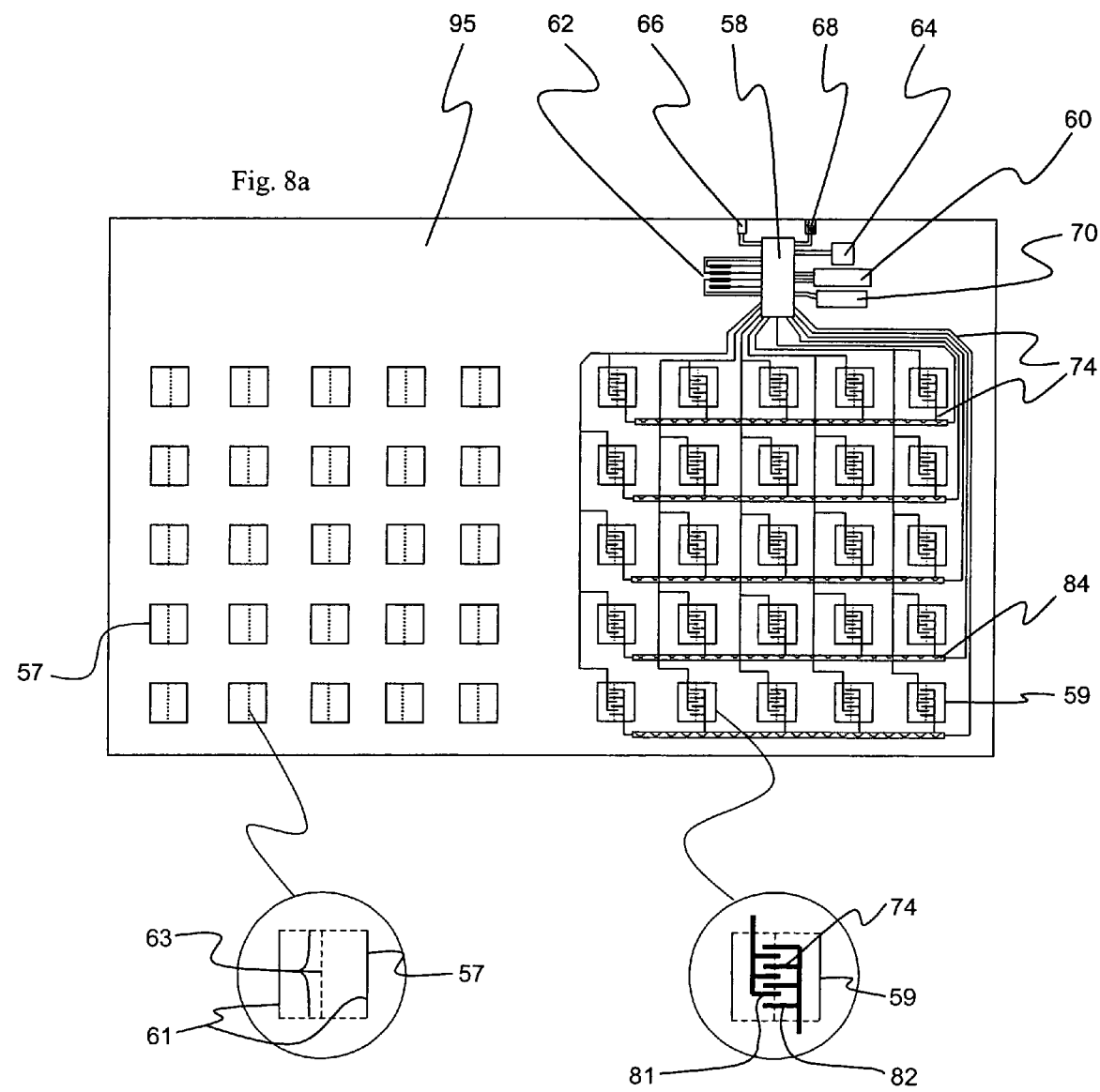

Referring to FIG. 8*a*, there is shown a laid open view of another embodiment of an electronic circuit board portion 95, which can be like the electronic circuit board portion 55 in FIG. 7*a*, including all of the electronic components and perforated openings 57, 59, and the only exception can be the omission of the tamper proof traces 72. Only dose removal conductive traces 74 are provided in this embodiment of the electronic circuit board 95, and the CPU 58 function is generally directed to a compliance mode, in regard to detecting the removal of each dose 11 of medication in a conventional manner, and as regards the proper time of each removal. In this "compliance only" embodiment, no tamper proof traces 74 are provided associated with the perforated openings 57 overlying the bubble chamber side of the blister pack 13. Only the perforated openings 59 on the right side (in the laid open view) of the electronic circuit board portion 95 have associated conductive traces, i.e., the dose removal traces 74.

The tamper proof traces 72 can be eliminated to make the electronic circuit board portion 95 less expensive to produce than the electronic circuit board portion 55 having the additional tamper proof traces 74. As stated above, this configuration can otherwise retains all of the capabilities described previously, except for the lack of anti-diversion related functions. This electronic circuit board portion 95 can be suitable for use where the medication contained in the package 1 is not of a type with which there is a concern regarding abuse or diversion of the medication. Thus, the electronic circuit board portion 55 in FIG. 7*a* would instead be used for medications with abuse potential such as analgesics, stimulants, and sedatives.

Mechanical and electronic details of the perforated openings on the electronic circuit board portion 95 are shown in FIGS. 8*b* and 8*c*, respectively. With the exception of the omission of the tamper proof traces 74, the perforated openings 57, 59 can be the same as shown in FIGS. 7*b* and 7*c*.

Referring now to FIGS. 9*a* and 9*b*, a dose removal is illustrated. The dose 11 removal procedure and path, is as heretofore described, i.e., via each of the aligned openings and perforated openings in each of the layers of the completed and assembled medication package 1. To remove a dose 11 of medication, the openings 7 in the child proof cover 3 must first be aligned with the perforated openings 9 in the front face of the outer packaging material 5, which can only be done by negotiating the child proof cover 3 and associated safety features. Once the openings 5 and perforated openings 9 are aligned, sufficient pressure must be applied to the perforated opening 9 to break through the perforated opening 9 and also break through the underlying perforated opening 57 in the upper side of the electronic circuit board portion 55 (or 95) which is lies above the bubble chamber 17 containing a dose 11 of medication. This pressure drives the dose 11 of medication contained in the bubble chamber 17 through the perforated opening 40 in the frangible layer 19, on the opposite side of the blister pack 13, and also through the perforated opening 59 in the lower side of the electronic circuit board portion 55 (or 95). Once through the perforated opening 59, the dose 11 of medication can fall freely from the medication package 1 onto an underlying support surface, such as a table or counter top, via openings 43 and 46 in each of the thin 31 and thick 33 circuit board spacers, and openings in the underside of the outer packaging material 5 and the rear surface of the child proof cover 3. Additional space can be created between the bottom of the child proof cover 3 and the underlying support surface by the feet 35 on the rear face of the child proof cover 3. The feet 35 provide added space between the support surface and the bottom of the child proof cover 3 for the dose 11 to drop completely through the medication package 1 onto the underlying support surface. In this way, the medication package 1 does not need to be lifted from the underlying support surface to fully remove a dose 11 of medication.

It should be noted that the heavy backing material 29 can provide added mechanical integrity, which can be a significant improvement over conventional blister packs with regard to dose removal. The heavy backing material 29 results in easier dose removal by eliminating package twisting and the misdirection of force as can commonly occurs with conventional blister packs. This can be particularly important for that segment of the patient population with, for example, tremors or arthritic hands.

Figure 10:
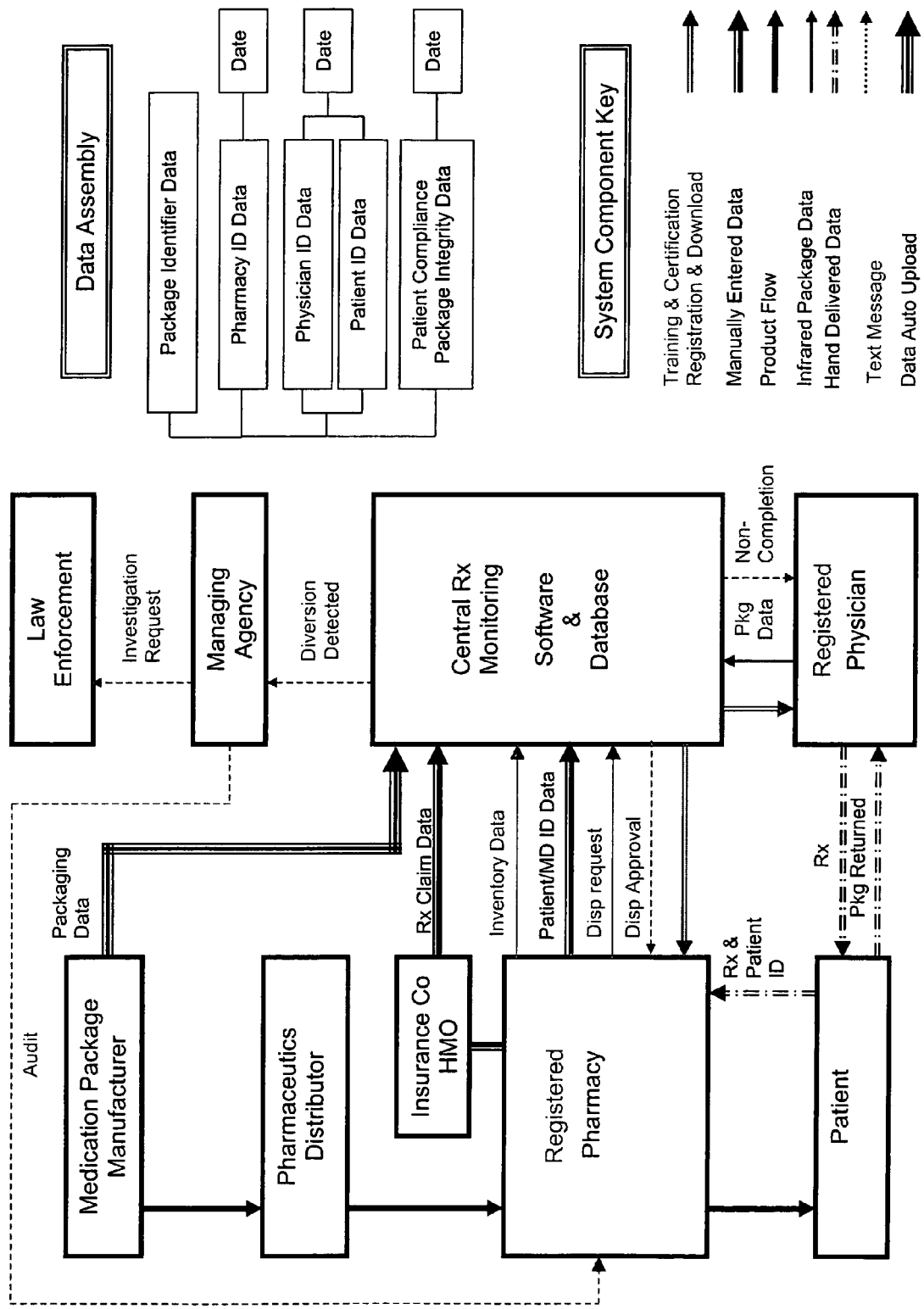
FIG. 10 is a logic diagram illustrating transmission, collection, and processing of data obtained by a medication package according to the invention.

Referring now to FIG. 10, there is diagrammatically illustrated an overview data flow, according to an embodiment of the invention, between the medication package 1 and various other locations/entities for implementing anti-diversion and compliance functions. This data flow can be employed to accomplish the objectives explained in more detail hereinafter. As shown, information flow can be configured between the medication package 1 and other sites, such as a central database, a database managing agency, a prescribing physician, a pharmacist, insurance providers, and law enforcement agencies. As shown, a system contemplated according to the invention can comprise, for example, the following features:

A central database, supervised by either a community, statewide or national agency, is established to receive, process and transmit data throughout the various system locations including pharmacies, physician offices, insurance companies, health maintenance organizations, and law enforcement agencies.

Each dispensing site (pharmacy) and each prescribing physician must, via the Internet, be trained, certified by, and register with the managing agency supervising the central database in order to download the software that will allow communication between the dispensing site or the physician, the central database and the dose 11 packages. This is especially important with the dispensing of medications with abuse potential, as these are commonly diverted to the illicit market. Each registered dispensing site will be assigned its own unique pharmacy registration number. Each registered physician can also be assigned a unique physician registration number, if so required.

One possible example of data flow assumes the drug manufacturer will utilize the proposed medication package 1 in the production process and load the pills at the manufacturing site and seal the packages for shipment to pharmaceutical distributors nationally. In this example, the central database will initially receive distribution data from the drug manufacturer in some automated fashion regarding the number of dose 11 packages manufactured and their unique sequential identifier information contained in the CPU 58, and the dates they were shipped.

When a registered dispensing site receives a certain number of the dose 11 packages, the unique data identifying each individual dose 11 package is sent via a specified form of data transmission, such as an infrared data output port on the dose 11 package to a personal computer or other such transmission device maintained by the dispensing site. This data is immediately and automatically transmitted via the Internet to the central database. Thus, inventory is established regarding the location of the unit and the current integrity of the dose 11 package.

In another possible application of this invention, the manufacturer will not use the package internally, and will ship its medication in bulk to pharmaceutical distributors and pharmacists. In this case the medication package 1 will be supplied to the pharmacists and loaded with doses 11 at the pharmacy. Therefore the flow of information in this example will begin at the local pharmacy. In either case the following description of events will occur.

When a patient presents a prescription to a registered dispensing site, the dispensing site relays encrypted information to the central database via the Internet. This encrypted information includes, automatically, the unique pharmacy identifier data, date and time, as well as manually entered data containing a unique patient identifier (e.g. social security number), and the prescribing physician's identifier data. The unique data identifying the individual dose 11 package to be dispensed is also entered into the central database via a specified form of data transmission, such as an infrared data output port, on the dose 11 package. The totality of this information represents a dispensing request.

The central database immediately compares the dispensing request data with current stored pharmacy and physician status data and any existing patient prescription or patient non-compliance history. Based on the outcome of a review by the central database of this current stored information, the central database will immediately transmit back to the requesting dispensing site, via the Internet, either a dispensing approval or denial, and such action will be recorded in the central database.

If approval is granted, the pharmacy will dispense the aforementioned dose 11 package to the patient. If dispensing is denied, the central database will categorize the reason(s) for the denial and this information will be automatically transmitted to the managing agency. If the reason for the denial is based on the condition of the dose 11 package, the ineligibility of the prescribing physician or the patient history, the pharmacy will automatically receive instructions from the central database.

If the patient who receives the medication presents insurance information to the pharmacy, a claim is submitted by the pharmacy to the patient's insurer according to their normal procedure. Periodically, when insurance company claims data is compared to central database information, diversion may be detected.

Each patient contracts with the prescribing physician to return the empty dose 11 package to the physician in order to receive a subsequent prescription renewal. This will allow the physician to determine if the doses 11 were removed from the dose 11 package according to the prescribed schedule.

Upon receiving the empty dose 11 package from the patient, the physician examines the package for indications of tampering and reviews the package compliance data. Thus, the physician will be able to identify possible diversion and also document those at risk for abuse if, for example, they removed the doses 11 more frequently than prescribed. The physician then sends the data containing the unique package identifier and the compliance data via a specified form of data transmission, such as an infrared data output port, to the central database via the Internet using a PC or similar device, and the central database records this information (hereafter referred to as completion data), as well as the time and date of said transmission.

The physician also will be provided with the capability to print a 'hard copy' of the patient's compliance data to place in the patient's permanent medical records.

If the central database does not receive the completion data from the prescribing physician within a predetermined time frame after the package dispensing date, this fact is recorded and a non-completion notice is automatically sent via the Internet to the physician.

If non-compliance or tampering has occurred and is therefore detected by the central database, or if patterns of non-completion develop, the managing agency may be automatically notified of possible abuse or diversion.

At all times the central database has an immediate record of how frequently any of its registered physicians are writing prescriptions for a particular medication, the physician's current registration status, how often and at which dispensing site each individual patient is obtaining prescriptions for the medication, the dispensing site's current registration status, and an accurate inventory of where all of the medications are located.

As prescribing, dispensing, compliance and completion data accumulates in the central database, over-prescribing physicians, patients who engage in "doctor-shopping" and those at risk for abuse can be quickly identified and investigative procedures can be initiated, as indicated.

Monthly inventory at dispensing sites is quickly accomplished by transferring data from each dose 11 package via a specified form of data transmission, such as an infrared data output port, to a PC or other transmission device, and then to the central database via the Internet.

The central database and associated software also allows for the random auditing of each registered dispensing site to determine whether the correct number of dose 11 packages is present and what the integrity of each dose 11 package is.

Therefore, according to the invention, and in accord with the foregoing description, a cooperative system of a medication package 1 having sensing, communication, data storage and data analysis features can be provided to help detect and deter non-compliance and diversion of medications. The medication package 1 described herein can provide audible and/or visual reminders of the prescribed dosing times to assure patient compliance with the prescribed dosing regimen. The medication package 1 can be a disposable package that is capable of transmitting data collected by or stored in system memory to other devices, such as remote computers, via wired or wireless transmission methods. The data can include, but need not be limited to, a unique medication package 1 identifier, individual dose removal history, which can include tamper events, and package integrity status. The medication package 1 can help ensure that doses cannot be removed in any fashion without the event being recorded, or the intrusion made obvious. The medication packaging system can also be inexpensively made, and can employ an electronic design that ensures the cost of the packaging relative to the cost of the medication is not prohibitive.

Personal computer based software can be provided to collect data from the medication package 1 and to facilitate communications with a central "Prescription Monitoring" (PM) database. An overall central database can utilize the software necessary to collect, process and transmit data between the various remote locations and the medication package 1. Information can be received and downloaded, for example via the internet, to and from a variety of locations, including physician offices, pharmacies, drug manufacturers, a managing agency, insurance companies, health maintenance organizations, and law enforcement agencies.

Additionally, software can be provided for the training, certification, and registration of pharmacies and physicians. Such training, certification, and registration can be made a prerequisite to the downloading of software to these sites to permit the transfer of data between these locations. The transmission of data via a specified form of data transmission can also be provided, for example via an infrared LED port, to transfer the data to a central data collection location, via a PC or similar device, to document and process pertinent information, including unique prescribing physician identifier data, unique patient identifier data, unique pharmacy identifier data, unique package identifier data, dose 11 removal history, and package integrity status. The central database can document the arrival date and integrity of each medication package 1 at each dispensing site when that data is transmitted to the dispensing site PC from each medication package 1, such as via a specified data transmission port, for example, an infrared output port. The central database can also contain drug manufacturer data reflecting the number of medication package 1s shipped to the pharmacy dispensing sites and the associated unique package identifier data. The central database software can compare the manufacturer data reflecting the number of medication package 1s shipped to the pharmacy dispensing sites, and the associated unique package identifier data, to the arrival date and integrity of each medication package 1 at the dispensing sites. In this manner, the inventory and status of each unique medication package 1 at the dispensing sites can be documented.

Preferably, the central database managing agency can have auditing capabilities, and can request, such as via the internet, any dispensing site to transmit the unique package identifier data and package integrity status contained in the inventory of a dispensing site, such as a pharmacy. Such data can be transmitted from the medication package 1 to a PC at the dispensing site (in the manner described above), and thence from the PC back to the central database, via the internet, for processing. The central database can further be programmed to perform a variety of functions, including, but not limited to, automatically notifying an overseeing, managing agency when a suspected diversion event occurs, allowing a dispensing pharmacy to manually enter, via a PC, unique prescribing physician identifier data and unique patient identifier data to the central database for processing, allowing this unique prescribing physician identifier data and unique patient identifier data to be combined with the associated unique package identifier information.

The central database, as well as associated dispensing sites and physician sites, can have software that provides for the encryption of all data transmission and storage, with the de-encryption of said data possible only by a managing agency in order to ensure confidentiality. A physician, such as at follow up office visits, can also enabled to review exactly when each dose was removed from the medication package 1 by displaying compliance data, such as obtained from the medication package 1, on an office PC.

The medication package 1 can also be designed to enable immediate transmission of data in real-time (reflecting the location and integrity of each specific medication package 1) between various system locations (pharmacies, physician offices, central database, a managing agency, drug manufacturer, and law enforcement agency), and can provide for the organization of a central PM database to receive and process the data. The medication package 1 can thus make it possible to:

Identify patients who are taking their legitimately obtained medications with abuse potential too frequently, thereby deterring addiction and/or diversion;

Identify those who simultaneously obtain multiple prescriptions for medications with abuse potential from various physicians, thereby detecting and deterring doctor shopping;

Identify physicians who over-prescribe medications with abuse potential, thereby identifying improper or illegal prescribing practices;

Provide for a tamper-proof electronic inventory system at all dispensing sites, thereby detecting and deterring pharmacy theft in a timely fashion;

Provide for the immediate transmission of prescription data from pharmacies to a central database. This data, when processed, would quickly reveal any discrepancies that may represent abuse and/or diversion and facilitate early investigative intervention;

Provide for the prerequisite training, certification and registration of all physicians and pharmacies with regard to accepted prescribing protocol; and Provide for auditing capabilities in order to detect illegal trends at all registered dispensing sites.

Ensure compliance of medications in that patient population who are predisposed to forget to take their medications as prescribed.

Data from the medication package 1 could be used at an individual physician's office solely to monitor compliance. The data could also be utilized at a community, state, or national level with the associated database to thwart the diversion of prescription medications. There are currently proposals by Congress and the Federal Drug Enforcement Agency (DEA) to establish a national PM program. The proposed database can readily be adapted to existing state prescription monitoring programs, and ones established in the future, if a form of data transmission is utilized that is compatible with the medication packaging system, such as, for example, infrared data transmission. The central database can contain software provisions for the interconnection of various community-based databases with each other and a statewide central database. Similarly, states using the proposed database at a statewide level can readily be adapted to communicate with a national PM program.

Although certain embodiments of the invention have been described in detail hereinabove, it will be appreciated by those skilled in the art that various modifications to those details could be developed in light of the overall teaching of the disclosure. Accordingly, the particular embodiments disclosed herein are intended to be illustrative only and not limiting to the scope of the invention which should be awarded the full breadth of the following claims and any and all embodiments thereof.

What is claimed is:

1. A medication package comprising:
  a. a blister pack having a first layer and a second layer, said first layer having a plurality of bubble chambers formed therein each adapted to receive a dose of medication, said second layer formed of a conductive frangible material, said second layer disposed adjacent said first layer and covering said plurality of bubble chambers such that said dose is removable from a bubble chamber by forcing said dose through said second layer;
  b. a circuit board having a first side adjacent said second layer, said first side having conductive dose removal traces, said conductive dose removal traces located adjacent said second layer in alignment with at least one of said plurality of bubble chambers, said conductive dose removal traces being a pair of separate dose removal traces associated with said at least one of said plurality of bubble chambers; and
  c. a CPU operably associated with said pair of separate dose removal traces, said CPU monitoring said pair of separate dose removal traces, and said CPU recording a dose removal event responsive to detecting a continuity between said pair of separate dose removal traces, said continuity resulting from said dose being removed through said second layer of said blister pack causing said second layer to contact both of said pair of separate dose removal traces such that said continuity results.

2. The medication package of claim 1 further comprising N rows and M columns of said dose removal traces, said N rows and M columns corresponding to respective ones of said pair of separate dose removal traces, wherein N×M doses are monitored by said CPU using N+M traces.

3. The medication package of claim 2 further comprising:
  a. overlapping portions of said N rows and M columns at intersections thereof; and
  b. insulating strips disposed intermediate said N rows and M columns at said overlapping portions.

4. The medication package of claim 1 further comprising a timer associated with said CPU, said timer tracking elapsed time from said dose being removed to identify when a subsequent dose is to be removed, and wherein said timer is initially activated responsive to detection of a first said continuity.

5. The medication package of claim 4 further comprising said CPU programmed with a preset dosing schedule specifying a time interval until said subsequent dose is to be removed.

6. The medication package of claim 1 further comprising a backing layer disposed adjacent said first layer of said blister pack, said backing layer having a plurality of openings located such that said plurality of bubble chambers are disposed through said plurality of openings, said backing layer having a thickness generally equal to a depth of said bubble chambers.

7. The medication package of claim 1 further comprising:
  a. said circuit board having a second side adjacent said first layer of said blister pack such that said blister pack is disposed between said first and second sides, said second side having conductive tamper proof traces, said conductive tamper proof traces located adjacent said first layer in alignment with at least one of said plurality of bubble chambers; and
  b. said CPU operably associated with said conductive tamper proof traces, said CPU monitoring said conductive tamper proof traces to detect a break in said conductive tamper proof traces, said break being at least one indicator of an attempt to remove said dose in an improper manner.

8. The medication package of claim 7 further comprising said tamper proof traces also provided on said second side of said circuit board.

9. The medication package of claim 8 further comprising:
  a. said first and second sides of said circuit board each having a front surface and a back surface, said front surface adjacent said second layer of said blister pack, and
  b. said tamper proof traces on each of said first and second sides of said circuit board being disposed on said back surface, and said dose removal traces being disposed on said front surface.

10. The medication package of claim 9 further comprising:
  a. said tamper proof traces and said dose removal traces having overlapping portions; and
  b. insulating strips separating said overlapping portions.

11. The medication package of claim 7 further comprising said conductive tamper proof traces provided around at least a portion of the periphery of the medication package, such that attempts to remove said dose in an unconventional manner will result in said break which will be detected by said CPU.

12. The medication package of claim 7 further comprising said CPU recording a detection of said break in said tamper proof trace as a tamper attempt if said continuity in said pair of separate dose removal traces is not detected within a predetermined time period subsequent to said break in said tamper proof trace.

13. The medication package of claim 1 further comprising:
  a. a data exchange port operably associated with said CPU for exchanging data between said CPU and an external device; and
  b. said data indicative of at least said continuities.

14. The medication package of claim 7 further comprising:
  a. a data exchange port operably associated with said CPU for exchanging data between said CPU and an external device; and
  b. said data indicative of at least one of said continuities and breaks.

15. The medication package of claim 7 further comprising a backing layer disposed adjacent said first layer of said blister pack, said backing layer having a plurality of openings located such that said plurality of bubble chambers are disposed through said plurality of openings, said backing layer having a thickness generally equal to a depth of said bubble chambers.

16. The medication package of claim 15 further comprising:
   a. each of said first and second sides of said circuit board having a plurality of openings, or perforated openings, aligned with said plurality of bubble chambers;
   b. a thin circuit board spacer intermediate said first side of said circuit board and said second layer of said blister pack;
   c. a thick circuit board spacer adjacent said first side of said circuit board on a side thereof opposite said thin circuit board spacer, such that said first side of said circuit board is intermediate said thin and thick circuit board spacers; and
   d. each of said thin and thick circuit board spacers having a plurality of openings, or perforated openings, aligned with said plurality of bubble chambers.

17. The medication package of claim 7 further comprising:
   a. a child proof cover enclosing at least a portion of said first and second sides of said circuit board and said first and second layers of said blister pack, said child proof cover having a plurality of openings, or perforated openings, in each of said front and rear faces, said child proof cover movable relative to said circuit board and said blister pack between first and second positions, said first position corresponding to a position at which said plurality of openings, or perforated openings are not aligned with said plurality of doses in said blister pack, said second position corresponding to a position at which said plurality of openings, or perforated openings are aligned with said plurality of doses in said blister pack; and
   b. at least one child proof feature restricting movement of said child proof cover between said first and second positions, said at least one child proof feature holding said child proof cover in said first position, said at least one child proof feature operable to permit said child proof cover to move to said second position.

18. The medication package of claim 17 wherein said at least on child proof feature comprises:
   a. a closure spring urging said child proof cover in said first position;
   b. at least one locking portion preventing movement of said child proof cover relative to said circuit board and said blister pack, said at least on locking portion movable to an unlocked position which permits movement of said child proof cover; and
   c. wherein said at least one locking portion must be moved to said unlocked position, said closure spring must be compressed to move said child proof cover to said second position, and said closure spring must be held in said compressed position to maintain said child proof cover in said second position until said dose is removed from said blister pack.

19. The medication package of claim 17 wherein said child proof features further comprise:
   a. an outer packaging material at least partially surrounding said circuit board and said blister pack, said outer packaging material disposed intermediate said circuit board and said child proof cover;
   b. at least one tab provided on at least one of said outer packaging material and said child proof cover; and
   c. at least one slot provided in at least one of said outer packaging material and said child proof cover, and said at least one tab slidably received in said at least one slot.

20. The medication package of claim 17 further comprising feet portions provided on said rear surface of said child proof cover, said feet portions adapted to support said child proof cover in a spaced apart relationship from an underlying surface on which said medication package may be placed to negotiate said child proof features and remove said dose.

21. A medication package comprising:
   a. a blister pack having a first layer and a second layer, said first layer having a plurality of bubble chambers formed therein each adapted to receive a dose of medication, said second layer formed of a conductive frangible material, said second layer disposed adjacent said first layer and covering said plurality of bubble chambers such that said dose is removable from a bubble chamber by forcing said dose through said second layer;
   b. a circuit board having a first side and a second side, each of said first and second sides having conductive traces, said blister pack disposed between said first and second sides with said first side adjacent said first layer and said second side adjacent said second layer, said conductive traces located on each of said first and second sides in alignment with at least one of said plurality of bubble chambers;
   c. said conductive traces on said first side of said circuit board being tamper proof traces, and said conductive traces on said second side of said circuit board being dose removal traces, said dose removal traces being a pair of separate dose removal traces associated with said at least one of said plurality of bubble chambers;
   d. a CPU operably associated with each of said tamper proof and said pair of separate dose removal traces, said CPU monitoring each of said tamper proof traces and said pair of separate dose removal traces to detect at least one of a break in said tamper proof traces and a continuity in said pair of separate dose removal traces, said CPU recording said breaks and said continuities;
   e. said break being an indicator of an attempt to remove said dose in an improper manner; and
   f. said continuity resulting from said dose being removed through said second layer of said blister pack causing said second layer to contact both of said separate dose removal traces such that said continuity results.

22. The medication package of claim 21 further comprising N rows and M columns of said dose removal traces, said N rows and M columns corresponding to respective ones of said pair of separate dose removal traces, wherein N×M doses are monitored by said CPU using N+M traces.

23. The medication package of claim 22 further comprising:
   a. overlapping portions of said N rows and M columns at intersections thereof; and
   b. insulating strips disposed intermediate said N rows and M columns at said overlapping portions.

24. The medication package of claim 21 further comprising a timer associated with said CPU, said timer tracking elapsed time from said dose being removed to identify when a subsequent dose is to be removed, and wherein said timer is initially activated responsive to detection of a first said continuity.

25. The medication package of claim 24 further comprising said CPU programmed with a preset dosing schedule specifying a time interval until said subsequent dose is to be removed.

26. The medication package of claim 21 further comprising a backing layer disposed adjacent said first layer of said blister pack, said backing layer having a plurality of openings located such that said plurality of bubble chambers are disposed through said plurality of openings, said backing layer having a thickness generally equal to a depth of said bubble chambers.

27. The medication package of claim 21 further comprising said tamper proof traces also provided on said second side of said circuit board.

28. The medication package of claim 27 further comprising:
 a. said first and second sides of said circuit board each having a front surface and a back surface, said front surface adjacent said second layer of said blister pack, and
 b. said tamper proof traces on each of said first and second sides of said circuit board being disposed on said back surface, and said dose removal traces being disposed on said front surface.

29. The medication package of claim 28 further comprising:
 a. said tamper proof traces and said dose removal traces having overlapping portions; and
 b. insulating strips separating said overlapping portions.

30. The medication package of claim 21 further comprising said tamper proof traces provided around at least a portion of the periphery of the medication package such that attempts to remove said dose in an unconventional manner will result in said break in said tamper proof trace which will be detected by said CPU.

31. The medication package of claim 21 further comprising said CPU recording a detection of said break in said tamper proof trace as a tamper attempt if said continuity in said pair of separate dose removal traces is not detected within a predetermined time period subsequent to said break in said tamper proof trace.

32. The medication package of claim 21 further comprising:
 a. a data exchange port operably associated with said CPU for exchanging data between said CPU and an external device; and
 b. said data indicative of at least one of said breaks and said continuities.

33. The medication package of claim 21 further comprising a backing layer disposed adjacent said first layer of said blister pack intermediate said first layer and said first side of said circuit board, said backing layer having a plurality of openings located such that said plurality of bubble chambers are disposed through said plurality of openings, said backing layer having a thickness generally equal to a depth of said bubble chambers.

34. The medication package of claim 33 further comprising:
 a. each of said first and second sides of said circuit board having a plurality of openings, or perforated openings, aligned with said plurality of bubble chambers;
 b. a thin circuit board spacer intermediate said second side of said circuit board and said second layer of said blister pack;
 c. a thick circuit board spacer adjacent said second side of said circuit board on a side thereof opposite said thin circuit board spacer, such that said second side of said circuit board is intermediate said thin and thick circuit board spacers; and
 d. each of said thin and thick circuit board spacers having a plurality of openings, or perforated openings, aligned with said plurality of bubble chambers.

35. The medication package of claim 21 further comprising:
 a. a child proof cover enclosing at least a portion of said first and second sides of said circuit board and said first and second layers of said blister pack, said child proof cover having a plurality of openings, or perforated openings, in each of said front and rear faces, said child proof cover movable relative to said circuit board and said blister pack between first and second positions, said first position corresponding to a position at which said plurality of openings, or perforated openings are not aligned with said plurality of doses in said blister pack, said second position corresponding to a position at which said plurality of openings, or perforated openings are aligned with said plurality of doses in said blister pack; and
 b. at least one child proof feature restricting movement of said child proof cover between said first and second positions, said at least one child proof feature holding said child proof cover in said first position, said at least one child proof feature operable to permit said child proof cover to move to said second position.

36. The medication package of claim 35 wherein said at least on child proof feature comprises:
 a. a closure spring urging said child proof cover in said first position;
 b. at least one locking portion preventing movement of said child proof cover relative to said circuit board and said blister pack, said at least on locking portion movable to an unlocked position which permits movement of said child proof cover; and
 c. wherein said at least one locking portion must be moved to said unlocked position, said closure spring must be compressed to move said child proof cover to said second position, and said closure spring must be held in said compressed position to maintain said child proof cover in said second position until said dose is removed from said blister pack.

37. The medication package of claim 35 wherein said child proof features further comprise:
 a. an outer packaging material at least partially surrounding said circuit board and said blister pack, said outer packaging material disposed intermediate said circuit board and said child proof cover;
 b. at least one tab provided on at least one of said outer packaging material and said child proof cover; and
 c. at least one slot provided in at least one of said outer packaging material and said child proof cover, and said at least one tab slidably received in said at least one slot.

38. The medication package of claim 35 further comprising feet portions provided on said rear surface of said child proof cover, said feet portions adapted to support said child proof cover in a spaced apart relationship from an underlying surface on which said medication package may be placed to negotiate said child proof features and remove said dose.

39. A method of recording at least one of proper and improper removal of a dose of medication from a medication package containing a blister pack, said blister pack having a first layer in which is formed a plurality of bubble chambers, each containing said dose of medication, and a second layer formed of a conductive frangible material covering said bubble chambers, a proper removal of said dose accomplished by pressing said dose through said conductive frangible material, and removal of said dose in any other manner being an improper removal, said medication package recording events indicative of said proper and improper removals of said dose, said method comprising:
  a. enclosing at least a portion of said blister pack in a circuit board member having first and second sides, said first side adjacent said first layer of said blister pack and said second side adjacent said second layer thereof;
  b. providing perforated openings in said first and second sides, said perforated openings aligned with said plurality of individual doses of medication;
  c. disposing a continuous conductive tamper proof trace on at least each of said perforated openings in said first side adjacent said first layer of said blister pack such that a break in said conductive tamper proof trace results in a detectable event;
  d. disposing a pair of separate conductive dose removal traces on each of said perforated openings in said second side adjacent said conductive frangible material of said blister pack such that removal of a dose through said frangible material creates a continuity between said pair of separate dose removal traces which is detectable;
  e. monitoring and recording events indicating at least one of said proper and improper dose removals;
  f. wherein a break in said tamper proof traces is an indicator of said improper dose removal;
  g. wherein a continuity between said pair of separate conductive dose removal traces is an indicator of said proper dose removal; and
  h. at least conveying data indicative of at least one of said proper and improper dose removal events from said medication package to an external device for analysis.

40. The method of claim 39 further comprising providing N rows and M columns of said dose removal traces, said N rows and M columns corresponding to respective ones of said pair of separate dose removal traces, wherein said monitoring is performed for N×M doses using N+M traces.

41. The method of claim 40 further comprising providing insulating strips intermediate overlapping portions of said N rows and M columns.

42. The method of claim 39 further comprising:
  a. recording elapsed time after each dose removal; and
  b. providing a preset dosing schedule specifying a time interval until a subsequent dose is to be removed.

43. The method of claim 42 further comprising initially activating said recording of elapsed time responsive to detection of a first said continuity.

44. The method of claim 39 further comprising additionally disposing said tamper proof traces on said second side of said circuit board.

45. The method of claim 44 further comprising additionally disposing said conductive tamper proof traces around at least a portion of a periphery of said medication package, such that attempts to remove said dose other than through said conductive frangible material will result in said break.

46. The method of claim 39 further comprising recording a detection of said break in said tamper proof trace as said indicator of an improper dose removal responsive to a failure to detect said continuity in said pair of separate dose removal traces within a predetermined time period subsequent to said break.

47. The method of claim 39 further comprising:
  a. enclosing at least a portion of said first and second sides of said circuit board in a child proof cover, said child proof cover having a plurality of openings, or perforated openings, said child proof cover movable relative to said circuit board between first and second positions, said first position corresponding to a position at which said plurality of openings, or perforated openings, are not aligned with said plurality of doses in said blister pack, said second position corresponding to a position at which said plurality of openings, or perforated openings, are aligned with said plurality of doses in said blister pack; and
  b. providing at least one child proof feature restricting movement of said child proof cover between said first and second positions, said at least one child proof feature holding said child proof cover in said first position, said at least one child proof feature operable to permit said child proof cover to move to said second position.

48. The method of claim 47 further comprising:
  a. providing a closure spring urging said child proof cover in said first position;
  b. providing at least one locking portion preventing movement of said child proof cover relative to said circuit board and said blister pack, said at least on locking portion movable to an unlocked position which permits movement of said child proof cover; and
  c. wherein said at least one locking portion must be moved to said unlocked position, said closure spring must be compressed to move said child proof cover to said second position, and said closure spring must be held in said compressed position to maintain said child proof cover in said second position until said dose is removed from said blister pack.

49. The method of claim 47 wherein further comprising:
  a. at least partially surrounding said circuit board and said blister pack with an outer packaging material such that said outer packaging material is disposed intermediate said circuit board and said child proof cover;
  b. providing at least one tab on at least one of said outer packaging material and said child proof cover; and
  c. providing at least one slot in at least one of said outer packaging material and said child proof cover such that said at least one tab is slidably received in said at least one slot.

50. The method of claim 47 further comprising providing feet portions on said child proof cover to support said child proof cover in a spaced apart relationship from an underlying surface on which said medication package may be placed to negotiate said child proof features and remove said dose.

* * * * *